US008247609B2

(12) United States Patent
Roques et al.

(10) Patent No.: US 8,247,609 B2
(45) Date of Patent: Aug. 21, 2012

(54) AMINOACID DERIVATIVES CONTAINING A DISULFANYL GROUP IN THE FORM OF MIXED DISULFANYL AND AMINOPEPTIDASE N INHIBITORS

(75) Inventors: Bernard Roques, Paris (FR); Marie-Claude Fournie-Zaluski, Paris (FR)

(73) Assignee: Pharamleads, Paris (FR)

( * ) Notice: Subject to any disclaimer, the term of this patent is extended or adjusted under 35 U.S.C. 154(b) by 868 days.

(21) Appl. No.: 12/146,941

(22) Filed: Jun. 26, 2008

(65) Prior Publication Data
US 2009/0012153 A1  Jan. 8, 2009

Related U.S. Application Data

(63) Continuation-in-part of application No. 12/084,091, filed as application No. PCT/EP2006/067711 on Oct. 24, 2006.

(30) Foreign Application Priority Data

Oct. 25, 2005  (FR) ..................................... 05 10862
May 5, 2006  (FR) ..................................... 06 04030

(51) Int. Cl.
C07C 321/00 (2006.01)
C07C 323/00 (2006.01)
C07C 381/00 (2006.01)
C07C 211/00 (2006.01)
A61K 31/38 (2006.01)

(52) U.S. Cl. .......................... 564/340; 564/463; 514/438

(58) Field of Classification Search ................. None
See application file for complete search history.

(56) References Cited

U.S. PATENT DOCUMENTS 4,618,708 A    10/1986   Roques et al.
(Continued)

FOREIGN PATENT DOCUMENTS

EP    0262053    3/1988
(Continued)

OTHER PUBLICATIONS

Silverman (The Organic Chemistry of Drug Design and Drug Action, 1992, Academic Press Inc.).*

(Continued)

*Primary Examiner* — Susanna Moore
*Assistant Examiner* — Jennifer C Sawyer
(74) *Attorney, Agent, or Firm* — Harness, Dickey & Pierce, P.L.C.

(57) ABSTRACT

The invention relates to novel compounds of formula (I): $H_2N-CH(R_1)-CH_2-S-S-CH_2-CH(R_2)-CONH-R_5$, wherein $R_1$ is a hydrocarbon chain, phenyl or benzyl radical, methylene radical substituted by a 5 or 6 atom heterocycle; $R_2$ is a phenyl or benzyl radical, a 5 or 6 atom aromatic heterocycle, methylene group substituted by a 5 or 6 atom heterocycle; $R_5$ is a $CH(R_3)-COOR_4$ radical, wherein $R_3$ is hydrogen, an OH or OR group, a saturated hydrocarbon group, a phenyl or benzyl radical and $OR_4$ is hydrophile ester, or 5 or 6 membered heterocycle comprising several heteroatoms selected from a group consisting of nitrogen, sulphur and oxygen, with at least two nitrogene atoms, wherein said heterocycle is substitutable by an alkyl $C_1$-$C_6$, phenyl or benzyl radical. The use of the inventive compounds in the form of drugs, a pharmaceutical composition comprising said compounds, a pharmaceutically acceptable excipient, the use in conjunction of at least one type of cannabinoid derivative for potentiating the analgesic and antidepressant effect of the novel compounds of formula (I) and/or morphine or the derivatives thereof are also disclosed.

35 Claims, 6 Drawing Sheets

U.S. PATENT DOCUMENTS

Figure 1:
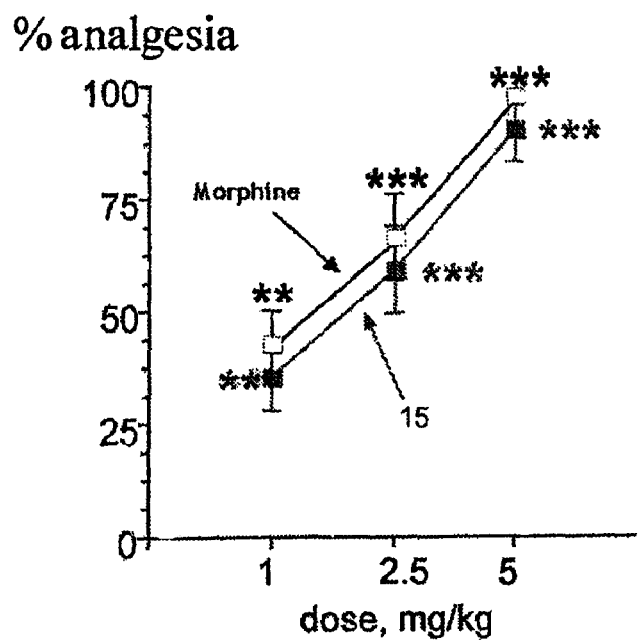

| | | | |
|---|---|---|---|
| 4,738,803 | A | 4/1988 | Roques et al. |
| 5,491,169 | A * | 2/1996 | Roques et al. ............ 514/529 |
| 2004/0242576 | A1 | 12/2004 | Flohr et al. |
| 2005/0025791 | A1 | 2/2005 | Remenar et al. |

FOREIGN PATENT DOCUMENTS

| | | |
|---|---|---|
| FR | 2 518 088 | 6/1983 |
| FR | 2 605 004 | 4/1988 |
| FR | 2 651 229 A | 3/1991 |

OTHER PUBLICATIONS

Marie-Claude Fournié-Zaluski et al.: "'Mixed Inhibitor-Prodrug' As a New Approach Toward Systemically Active Inhibitors of Enkephalin-Degrading Enzymes", Journal of Medicinal Chemistry, American Chemical Society. Washington, US, vol. 35, No. 13, 1992, pp. 2473-2481, XP002019768, ISSN: 0022-2623.

Florence Noble et al.: "Inhibition of the Enkephalin-Metabolizing Enzymes by the First Systemically Active Mixed Inhibitor Prodrug RB 101-Induces Potent Analgesic Responses in Mice and Rats", Journal of Pharmacology and Experimental Therapeutics, American Society for Pharmacology and, US, vol. 261, No. 1, Jan. 1992, pp. 181-190, XP000386321, ISSN: 0022-3565.

Florence Noble et al.: "Pain-Suppressive Effects on Various Nociceptive Stimuli (Thermal, Chemical, Electrical and Inflammatory) of the First Orally Active Enkephalin-Metabolizing Enzyme Inhibitor RB 120", Pain, 73 (1997) 383-391 Coden: PAINDB; ISSN:0304-3959, 1997, XP002386725.

C. Schmidt et al.: "Analgesic Responses Elicited by Endogenous Enkephalins (protected by Mixed Peptidase Inhibitors) in a Variety of Morphine-Sensitive Noxious Tests", European Journal of Pharmacology, 192 (1991), pp. 253-262, 1991 Elsevier Science Publishers B.V. (Biomedical Division) 0014-2999/91, EJP 51646.

Marie-Claude Fournié-Zaluski et al. : "Analgesic Effects of Kelatorphan, a New Highly Potent Inhibitor of Multiple Enkephalin Degrading Enzymes", European Journal of Pharmacology, 102 (1984) pp. 525-528.

Gilles Waksman et al. "In Vitro and in Vivo Effects of Kelatorphan on Enkephalin Metabolism in Rodent Brain", European Journal of Pharmacology, 117 (1985) 233-243.

R. Maldonado et al. : "Comparison of Selective and Complete Inhibitors of Enkephalin-Degrading Enzymes on Morphine Withdrawal Syndrome", European Journal of Pharmacology, 165 pp. 199-207, received Dec. 8, 1988, revised MS received Mar. 2, 1989, accepted Mar. 28, 1989, EJP 50832.

V. Kayser et al. : "Potent Antinociceptive Effects of Kelatorphan (a Highly Efficient Inhibitor of Multiple Enkephalin-Degrading Enzymes) Systemically Administered in Normal and Arthritic Rats", Brain Research, 497 (1989) pp. 94-101, BRES 14785.

Huixiong Chen et al. : "Phosphinic Derivatives as New Dual Enkephalin-Degrading Enzyme Inhibitors: Synthesis, Biological Properties, and Antinociceptive Activities", Journal of Medicinal Chemistry, 2000, vol. 43, pp. 1398-1408.

Huixiong Chen et al. : "Long Lasting Antinociceptive Properties of Enkephalin Degrading Enzyme (NEP and APN) Inhibitor Prodrugs", Journal of Medicinal Chemistry, 2001, vol. 44, No. 21, pp. 3523-3530.

Bernard P. Rogues et al. : "Neutral Endopeptidase 24.11: Structure, Inhibition, and Experimental and Clinical Pharmacology", The American Society for Pharmacology and Experimental Therapeutics, 1993, vol. 45, No. 1, pp. 87-133.

B. Malfroy et al. : "High-Affinity Enkephalin-Degrading Peptidase in brain is Increased After Morphine", Nature vol. 276, Nov. 30, 1978, pp. 523-526.

* cited by examiner

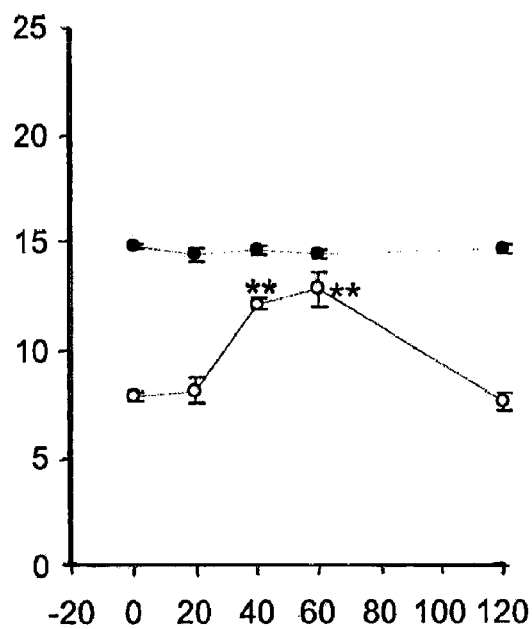
Fig. 6A
Fig. 6B
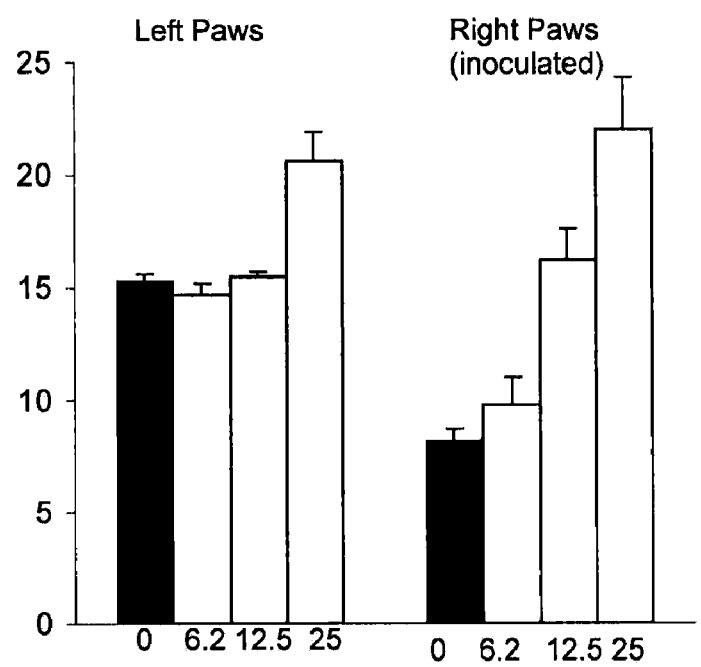

AMINOACID DERIVATIVES CONTAINING A DISULFANYL GROUP IN THE FORM OF MIXED DISULFANYL AND AMINOPEPTIDASE N INHIBITORS

CROSS REFERENCE TO RELATED APPLICATIONS

This application is a continuation-in-part application of U.S. Ser. No. 12/084,091, filed Apr. 24, 2008, which is a National Phase Entry of PCT Application Serial No. PCT/EP2006/067711, filed Oct. 24, 2006, which claims priority to French Application Serial No. 05/10862, filed Oct. 25, 2005 and French Application Serial No. 06/04030, filed May 5, 2006. The entire disclosures of the above applications are incorporated herein by reference.

BACKGROUND AND SUMMARY

The invention relates to novel mixed inhibitors of the neprilysin and aminopeptidase N.

It is known that natural opioid peptides or enkephalins—(Tyr-Gly-Gly-Phe-Met or Tyr-Gly-Gly-Phe-Leu)—are primarily degraded by two zinc metallopeptidases, neprilysin (EC 3.4.24.11) which cleaves the Gly3-Phe4 bond (Nature 276 (1978) 523) and aminopeptidase N (EC 3.4.11.2) which cuts the Tyr1-Gly2 bond of these peptides (Eur. J. Pharmacol. 117 (1985) 233; review in Pharmacological Review., 1993, 45, 87-146). Mixed inhibitors of these two enzymes are known, by completely protecting endogenous enkephalins from enzymatic degradation, they reveal the pharmacological activities, in particular analgesic and antidepressant activities, of enkephalins. Mixed inhibitors, described in the prior art, of these two enzymatic activities are compounds with a hydroxamate function (FR 2 518 088 and FR 2 605 004), aminophosphinic compounds (FR 2 755 135 and FR 2 777 780) and amino acid derivatives (FR 2 651 229). The compounds divulged in these patent applications exhibit excellent in vitro and in vivo activity after administration by intracerebroventricular route; this was particularly demonstrated in the case of the hydroxamates (Eur. J. Pharmacol., 102, (1984), 525-528; Eur. J. Pharmacol., 165, (1989), 199-207; Eur. J. Pharmacol, 192, (1991), 253-262), for which significant activity also could be demonstrated after intravenous (IV) administration in a model of rat arthritis (Brain Research, 497, (1989), 94-101). In the case of aminophosphinic derivatives and amino acid derivatives, good in vivo activity was demonstrated after administration by IV route when the molecules studied were solubilized in a mixture of oil, ethanol and water (J. Med. Chem., 43, (2000), 1398-1408; J. Med. Chem., 44, (2001), 3523-3530; J. Pharm. Exp. Ther., 261, (1992), 181-190). However, even if one of the compounds belonging to the series of amino acid derivatives proved relatively water soluble (Pain, 73, (1997), 383-391), none the molecules previously divulged exhibits solubility in an aqueous phase and sufficient bioavailability to be administered by oral route and to provide advantageous analgesic responses to sufficiently low doses in animals to be adapted to man. Similarly, none the molecules previously cited allows intravenous administration since in animal tests they require solubilization in mixtures incompatible with administration by this route in man.

One of the objects of the invention is to provide novel water-soluble compounds capable of jointly inhibiting the two enzymatic activities responsible for the degradation of enkephalins and to manifest their pharmacological properties after dissolution in an aqueous solvent and intravenous, subcutaneous, percutaneous, intrathecal or intra-articular injection and by oral or nasal route.

It is generally understood that the hematoencephalic barrier is more easily crossed by hydrophobic and non-polar molecules. However, unexpectedly, the hydrophilic molecules that have been synthesized exhibit powerful responses in central tests indicating the existence of a good capacity to reach cerebral structures by several administration routes (except for the local route). Another object of the invention is to provide novel compounds that exhibit the properties of morphine substances, in particular analgesia, beneficial effects on behavior (reduction in the emotional component of pain and antidepressant responses) and peripheral effects (antidiarrheal, antitussive, anti-inflammatory) without their major disadvantages (tolerance, physical and psychological dependence, respiratory depression, constipation, nausea).

Moreover, inflammatory and neurogenic pain, whose peripheral component is significant, are reduced or even eliminated by the compounds according to the invention administered by oral route and thus without such compounds being constrained from reaching the central nervous system. This result, highly advantageous but unexpected, was formally demonstrated by the use of an antagonist incapable of entering the brain. This completely reduces all of the effects due to stimulation of cerebral opioid receptors by the compounds according to the invention, without altering the analgesics effects of the compounds on these types of pain, in particular neurogenic pain.

Most notably, the invention relates to compounds of following formula (I):

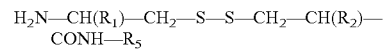

$H_2N—CH(R_1)—CH_2—S—S—CH_2—CH(R_2)—CONH—R_5$ wherein:

$R_1$ represents:
  a hydrocarbon chain, saturated or unsaturated, linear or branched, comprising from 1 to 6 carbon atoms, optionally substituted by:
    an OR, SR or S(O)R radical, wherein in each of these radicals R represents a hydrogen, a linear or branched hydrocarbon chain of 1 to 4 carbon atoms, a phenyl or benzyl radical,
    a phenyl or benzyl radical,
  a phenyl or benzyl radical optionally substituted by:
    1 to 5 halogens, notably fluorine,
    an OR, SR or S(O)R radical, wherein in each of these radicals R is defined as above,
  a methylene radical substituted by a 5- or 6-atom heterocycle, aromatic or saturated, having as a heteroatom an atom of nitrogen or sulfur, optionally oxidized in the form of N-oxide or S-oxide;

$R_2$ represents:
  a phenyl or benzyl radical, optionally substituted by:
    1 to 5 halogen atoms, notably fluorine,
    an OR or SR radical, wherein in each of these radicals R is defined as above,
    an amino group optionally mono- or di-substituted by an aliphatic, cyclic or linear group of 1 to 6 carbon atoms,
  a 5- or 6-atom aromatic ring,
  a 5- or 6-atom aromatic heterocycle, the heteroatom being oxygen, nitrogen or sulfur,
  a methylene group substituted by a 5- or 6-atom heterocycle, aromatic or saturated, the heteroatom being oxygen, nitrogen or sulfur, the nitrogen and sulfur atoms possibly being oxidized in the form of N-oxide or S-oxide.

$R_5$ represents:

a) a $CH(R_3)$—$COOR_4$ radical wherein $R_3$ represents:
- hydrogen,
- an OH or OR group, with R as defined above,
- a saturated hydrocarbon chain (alkyl), linear or branched, comprising from 1 to 6 carbon atoms, optionally substituted by an OR or SR radical, wherein in each of these radicals R is defined as above,
- a phenyl or benzyl radical, optionally substituted by:
  - 1 to 5 halogens, notably fluorine,
  - an OR or SR radical, with R as defined above. and $OR_4$ represents
- an $OCH_2COOR'$ glycolate or $OCH(CH_3)COOR'$ lactate radical, wherein in each of these radicals R' represents
  - a saturated hydrocarbon chain (alkyl) with 1 to 6 carbon atoms, linear or branched and optionally substituted by an alkoxy group at C1 to C3, preferably an alkyl group at C1-C4 optionally substituted by a methoxy group,
  - a cycloalkyl group at $C_5$-$C_8$, preferably a cycloalkyl group at $C_5$-$C_6$,
  - a phenyl, benzyl, heteroaryl, alkylheteroaryl group,
- an $OCH(R'')O(CO)OR'$ or $OCH(R'')O(CO)R'$ group, wherein in each of these radicals R' is defined as above and R'' represents
  - a hydrogen atom,
  - a C1-C6 alkyl chain, linear or branched, optionally substituted by a C1-C3 alkoxy group, preferably a C1-C4 alkyl group optionally substituted by a methoxy group,
  - a C5-C8 cycloalkyl group, preferably a C5-C6 cycloalkyl group,
  - a phenyl, benzyl, heteroaryl, alkylheteroaryl group,
- an $OCH(CH_2OCOR')_2$ or $OCH_2$—$CH(OCOR')$—$CH_2OCOR'$ triglyceride radical, wherein in each of these radicals R' is defined as above,
- a glycoside radical such as D-glucose, β-D-glucopyranose, α- or β-galactopyranose,
- an $OCH_2CH_2(SO_2)CH_3$ sulfonate radical,
- an $OCH(CH_2OH)_2$ radical;

b) a 5- or 6-link heterocycle comprising several heteroatoms selected from the group comprised of nitrogen, sulfur and oxygen, of which 2 atoms are nitrogen, said heterocycle possibly being substituted by a C1-C6 alkyl, phenyl or benzyl radical;

as well as additive salts of the aforesaid compounds (I) with pharmaceutically acceptable mineral or organic acids.

The invention also has as an object additive salts of compounds of formula (I), obtained with pharmacologically acceptable organic or mineral acids such as phosphates, hydrochloride, acetate, methanesulfonate, borate, lactate, fumarate, succinate, hemisuccinate, citrate, tartrate, hemitartrate, maleate, ascorbate, hemifumarate, hexanoate, heptanoate, hippurate, hydrocinnamate, phenylglyoxylate and nicotinate.

Within the framework of the present invention, the expression "hydrocarbon chains" designates alkanes, alkenes or alkynes. Notably, the expression "saturated hydrocarbon chains" designates alkyl radicals comprising from 1 to 6 carbon atoms (C1-C6) or from 1 to 4 carbon atoms (C1-C4), linear or branched. Examples of alkyl radicals comprising from 1 to 4 carbon atoms include methyl, ethyl, propyl, butyl, isopropyl, 1-methyl-ethyl, 1-methyl-propyl and 2-methyl-propyl radicals. Examples of alkyl radicals comprising from 1 to 6 carbon atoms further include pentyl, hexyl, 1-methyl-butyl, 1-methyl-pentyl, 2-methyl-butyl, 2-methyl-pentyl, 3-methyl-butyl, 3-methyl-pentyl, 4-methyl-pentyl or 1-ethyl-propyl, 1-ethyl-butyl and 2-ethyl-butyl radicals. The expression "unsaturated hydrocarbon chains" designates alkenyl radicals (at least one double bond), for example vinyl, allyl or similar, or alkynyl (at least one triple bond) comprising from 2 to 6 atoms of carbon, or 2 to 4 carbon atoms, linear or branched.

The term "halogen" used herein designates chlorine, bromine, iodine or fluorine.

As non-limiting example of heterocyclic cores with 5 or 6 atoms, aromatic or saturated, having as a heteroatom an atom of nitrogen or sulfur, the following radicals can be cited: thienyl, pyrrolyl, imidazolyl, pyrazolyl, isothiazolyl, pyridyl, pyrazinyl, pyrimidinyl, pyridazinyl, pyrrolidinyl, pyrrolinyl, imidazolidinyl, pyrazolidinyl, pyrazolinyl, piperidyl, piperazinyl, thiadiazolyle, the nitrogen and sulfur atoms optionally being oxidized in the form of N-oxide or S-oxide.

As non-limiting example of heterocyclic cores with 5 or 6 atoms, aromatic or saturated, having as a heteroatom an atom of oxygen, the following radicals can be cited: furyl, pyranyl, isoxazolyl, morpholinyl, furazanyl, oxazolyl, oxazolidinyl and oxazolinyl.

Radical $R_1$ advantageously represents an alkyl radical having from 1 to 4 atoms of carbon, optionally substituted by an OR, SR or S(O)R radical, wherein in each of these radicals R is defined as above. $R_1$ represents even more advantageously an alkyl radical having from 1 to 4 carbon atoms substituted by a SR radical, with R defined as above, notably with R representing a saturated hydrocarbon chain, linear or branched, with 1 to 4 atoms of carbon.

Radical $R_2$ advantageously represents:
- a benzyl or phenyl radical,
- a methylene radical substituted by a 5- or 6-atom heterocycle, aromatic or saturated, having as a heteroatom an atom of nitrogen or sulfur, optionally oxidized in the form of N-oxide or S-oxide.

Notably, radical $R_2$ represents a benzyl radical or a methylene radical substituted by a 5- or 6-atom heterocycle, aromatic or saturated, having as a heteroatom a sulfur or nitrogen atom, optionally oxidized in the form of N-oxide or S-oxide, even more advantageously a benzyl radical or a methylene radical substituted by a thiophenyl radical (thienyl).

Radical $R_5$ is a radical that increases the hydrophilic character of the whole molecule, which normally is a rather hydrophobic molecule.

According to a first embodiment of the invention, radical $R_5$ represents a $CH(R_3)$—$COOR_4$ radical.

In this first embodiment, radical $R_3$ advantageously represents a hydrogen atom or an alkyl radical having from 1 to 6 carbon atoms, even more advantageously 1 to 4 carbon atoms, optionally substituted by an OR or SR radical, wherein in each of these radicals R is defined as above. Radical $R_3$ even more advantageously represents a hydrogen atom or an alkyl radical having from 1 to 6 carbon atoms, even more advantageously 1 to 4 carbon atoms, substituted by an OH or SH radical.

Radical $OR_4$ advantageously represents:
- an $OCH_2COOR'$ glycolate radical, with R' as defined above (notably R' represents a C1-C4 alkyl group optionally substituted by a methoxy group or a C5-C6 cycloalkyl group),
- an $OCH(R'')O(CO)OR'$ or $OCH(R'')O(CO)R'$ radical, with R' and R'' as defined above (notably R' and/or R'' represent a C1-C4 alkyl group optionally substituted by a methoxy group or a C5-C6 cycloalkyl group or R'' represents a hydrogen atom), an OCH(CH₂OCOR')₂ or OCH₂—CH(OCOR')—CH₂OCOR' triglyceride radical, wherein in each of these radicals R' is defined as above, a glycoside radical such as D-glucose, an OCH₂CH₂(SO₂)CH₃ sulfonate radical, an OCH(CH₂OH)₂ radical.

Notably, radical OR₄ represents an OCH(R")O(CO)OR' or OCH(R")O(CO)R' group, the R' radical representing a C1-C4 alkyl chain (notably an ethyl radical) and the R" radical representing a methyl, CH(CH₃)₂, cyclohexyl or phenyl radical.

According to a second embodiment of the invention, radical R₅ represents a heterocycle, of 5 or 6 links, comprising several heteroatoms, selected among the group comprising nitrogen, sulfur and oxygen, of which 2 atoms are nitrogen, said heterocycle possibly substituted by a C1-C6 alkyl radical or a phenyl or benzyl radical.

In said second embodiment, the heterocycle is advantageously a 5-link heterocycle comprising 2 nitrogen atoms, optionally substituted by a C1-C4 alkyl chain, notably 2-ethyl-1,3,4-thiadiazole.

The invention notably relates to the following compounds:

1-(2-(1-(2,3-diacetoxypropoxycarbonyl)-ethylcarbamoyl)-3-thiophen-3-ylpropyldisulfanylmethyl)-3-methylsulfanylpropyl-amine, 1-(2-(1-(2-methanesulfonylethoxycarbonyl)-ethylcarbamoyl)-3-thiophen-3-ylpropyldisulfanylmethyl)-3-methylsulfanylpropyl-amine, 1-(2-(1-(1-ethoxycarbonyloxyethoxycarbonyl))-ethylcarbamoyl)-3-thiophen-3-yl-propyldisulfanylmethyl)-3-methylsulfanylpropyl-amine, 1-(2-(1-ethoxycarbonylmethyloxycarbonylethylcarbamoyl)-3-thiophen-3-yl-propyldi sulfanylmethyl)-3-methylsulfanylpropyl-amine, 1-(2-(1-(1-ethoxycarbonyloxyethoxycarbonyl)-2-hydroxypropylcarbamoyl)-3-thiophen-3-ylpropyldisulfanylmethyl)-3-methylsulfanylpropyl-amine, 1-(2-(1-(2-acetoxy-1-acetoxymethylethoxycarbonyl)-ethylcarbamoyl)-3-thiophen-3-ylpropyldisulfanylmethyl)-3-methylsulfanylpropyl-amine, 1-(2-(1-(2-hydroxy-1-hydroxymethylethoxycarbonyl)-ethylcarbamoyl)-3-thiophen-3-ylpropyldisulfanylmethyl)-3-methylsulfanylpropyl-amine, 1-(2-(1-(3,4,5,6-tetrahydroxytetrahydropyran-2-ylmethoxycarbonyl)-ethylcarbamoyl)-3-thiophen-3-yl-propyldisulfanylmethyl)-3-methylsulfanylpropyl-amine, 1-(2-(1-(1-ethoxycarbonyloxy-ethoxycarbonyl)-2-hydroxypropylcarbamoyl)-3-phenylpropyldisulfanylmethyl)-3-methylsulfanylpropyl-amine, 1-(2-(1-(2-acetoxy-1-acetoxymethyl-ethoxycarbonyl)-2-hydroxypropylcarbamoyl)-3-phenylpropyldisulfanylmethyl)-3-methylsulfanylpropyl-amine, 1-(2-((1-ethoxycarbonyloxy-ethoxycarbonylmethyl)-carbamoyl)-3-phenyl-propyldisulfanylmethyl)-3-methylsulfanylpropyl-amine, 3-(2-amino-4-methylsulfanyl-butyldisulfanyl)-2-benzyl-N-(5-ethyl-(1,3,4)-thiadiazol-2-yl)-propionamide, 1-(2-((1-ethoxycarbonyloxy-2-methyl-propoxycarbonylmethyl)-carbamoyl)-3-phenyl-propyldisulfanylmethyl)-3-methylsulfanyl-propyl-amine, 1-(2-((cyclohexyl-ethoxycarbonyloxy-methoxycarbonylmethyl)-carbamoyl)-3-phenyl-propyldisulfanylmethyl)-3-methylsulfanyl-propyl-amine, 1-(2-((ethoxycarbonyloxy-phenyl-methoxycarbonylmethyl)-carbamoyl)-3-phenyl-propyldisulfanylmethyl)-3-methylsulfanyl-propyl-amine, 3-methylsulfanyl-1-(3-phenyl-2-((1-propionyloxy-ethoxycarbonylmethyl)-carbamoyl)-propyldisulfanylmethyl)-propyl-amine, 1-(2-((2-methyl-1-propionyloxy-propoxycarbonylmethyl)-carbamoyl)-3-phenyl-propyldisulfanylmethyl)-3-methylsulfanyl-propyl-amine, 1-(2-((cyclohexyl-propionyloxy-methoxycarbonylmethyl)-carbamoyl)-3-phenyl-propyldisulfanylmethyl)-3-methylsulfanyl-propyl-amine, 3-methylsulfanyl-1-(3-phenyl-2-((phenyl-propionyloxy-methoxycarbonylmethyl)-carbamoyl)-propyldisulfanylmethyl)-propyl-amine.

The compounds of formula (I) potentially have from 2 to 9 centers of asymmetry. Radicals $R_1$, $R_2$ and $R_3$ will be introduced in such a way as to obtain optically pure chains corresponding to stereochemistry recognized by enzymatic activities. Radicals $R_4$ optionally contain an unresolved center of asymmetry.

The compounds of formula (I) are obtained:

1) by condensation of a protected beta-aminothiol on the amino function by a t-butyloxycarbonyl (Boc) group (II) with a mercaptoalcanoic acid (III) by means of methoxycarbonylsulfonyl chloride in solution in THF (tetrahydrofuran), leading to IV.

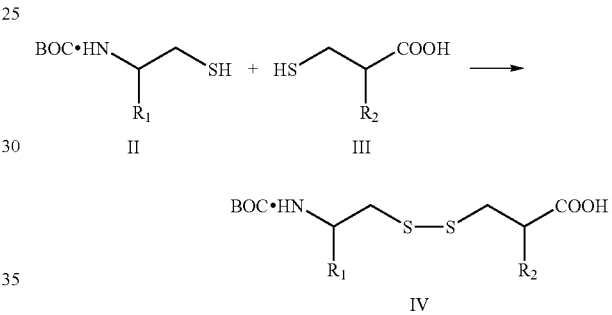

Boc beta-aminothiol II is prepared from the corresponding commercial Boc amino acid of absolute configuration S with retention of configuration according to a method well-known by those skilled in the art (J. Med. Chem., 35, (1992) 1259).

The mercaptoalcanoic acid III is obtained from the corresponding methyl malonate monoester V, which, according to a method well-known by those skilled in the art (Ber., 57, (1924), 1116) is transformed into acrylate VI.

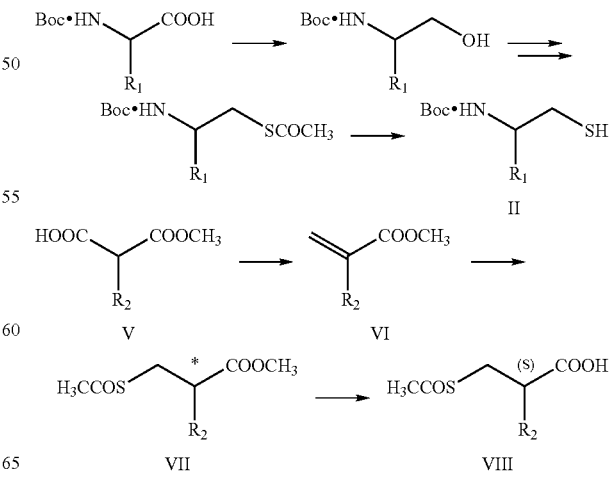

The addition of thioacetic acid to acrylate VI leads to racemic derivative VII (Biochemistry, 16, (1977), 5484). Resolution by alpha-chymotrypsin isolates the optically pure acetylthioacide VIII (Bioorg. Med. Chem. Let, 3, (1993), 2681). Alkaline hydrolysis of the thioester leads to compound III.

2) The compounds of formula (I), wherein radical $R_5$ represents a $CH(R_3)$—$COOR_4$ radical, can be obtained by the following synthetic pathways.

2.1) Dissymmetrical disulfide IV is coupled, under conventional peptide coupling conditions, with aminoester IX, leading to the protected inhibiter X.

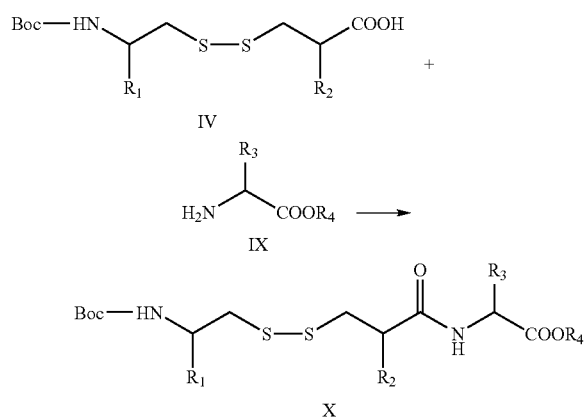

According to an alternative method, compounds X can be obtained by condensation, by means of methoxycarbonyl sulfenyl chloride, of Boc-β-aminothiol II with a mercaptoacylaminoester of formula XI.

Mercaptoacyl aminoester XI is prepared from compound III. It is oxidized by an ethanolic iodine solution into disulfide XII. Compound XII is coupled under conventional peptide coupling conditions with aminoester IX, leading to XIII. Treatment of XIII with a reducing agent such as the mixture 3 N Zn+HCl, releases compound XI.

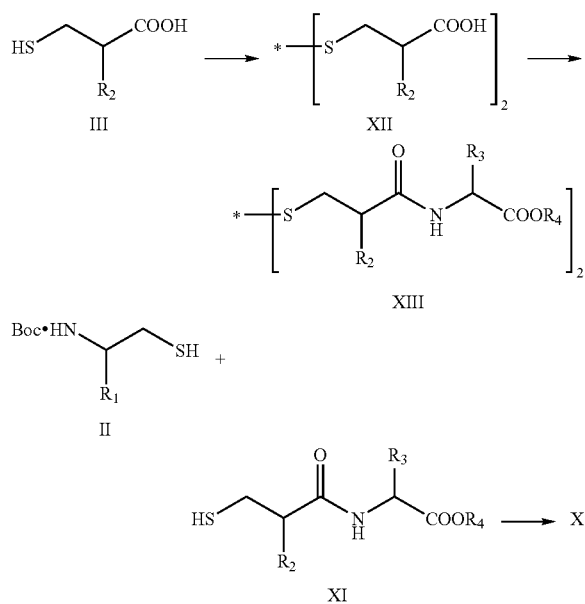

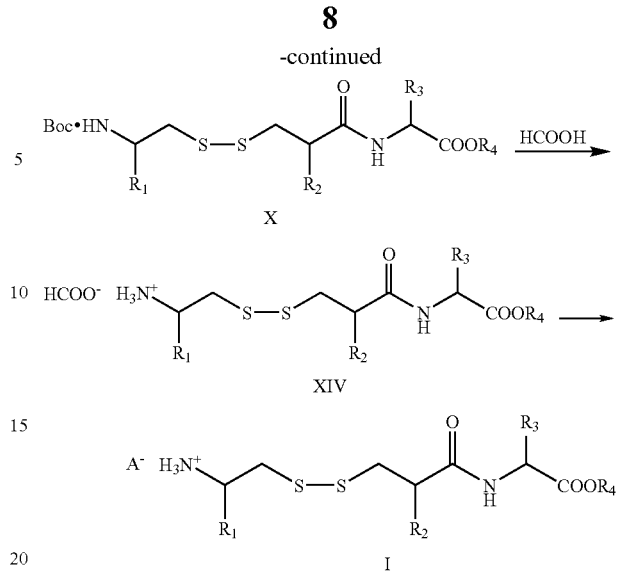

The N-terminal Boc group of X is cut by the action of formic acid, releasing XIV. The counter-ion of XIV is changed quantitatively by treatment with one equivalent of 0.1 M NaHCO$_3$, extraction in an organic medium (EtOAc) of the compound possessing a free amino function, then addition of one equivalent of the organic acid or mineral chosen to lead to I.

2.2) Aminoester IX is obtained by condensation of Boc amino acid XII with alcohol $R_4OH$, then deprotection by trifluoroacetic acid (TFA) and neutralization by soda. If alcohol $R_4OH$ is a primary alcohol, coupling with XII is carried out under conventional conditions (1-[3-(dimethylamino) propyl]-3-ethylcarbodiimide hydrochloride (EDCI), 1-hydroxybenzotriazole hydrate (HOBt) or activated ester). If alcohol $R_4OH$ is a secondary alcohol, condensation is achieved via a Mitsunobu reaction (Synthesis (1981) 1-28), using the mixture diethyl azodicarboxylate/triphenyl phosphine (DEAD/PPhe$_3$).

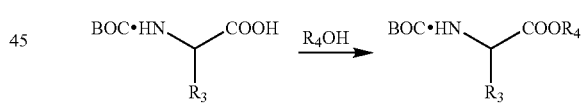

Alcohols $R_4OH$ are in most cases commercial compounds. When $R_4OH$ is an alcohol leading to an ester "cascade," it is synthesized from methods described in the literature.

2a) Compounds of formula (I), wherein radical $R_5$ represents a heterocycle radical such as defined above, can be obtained by the following synthetic pathways.

2.a.1)

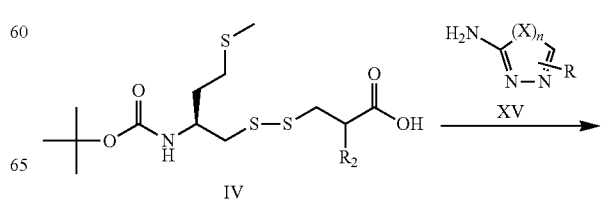

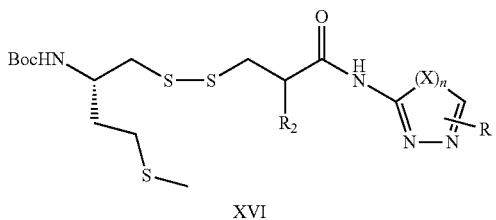

XVI

Dissymmetrical disulfide IV is coupled under conventional peptide coupling conditions with amino heterocycle XV to lead to XVI. Deprotection of the Boc group is carried out as above leading to derivative XVII.

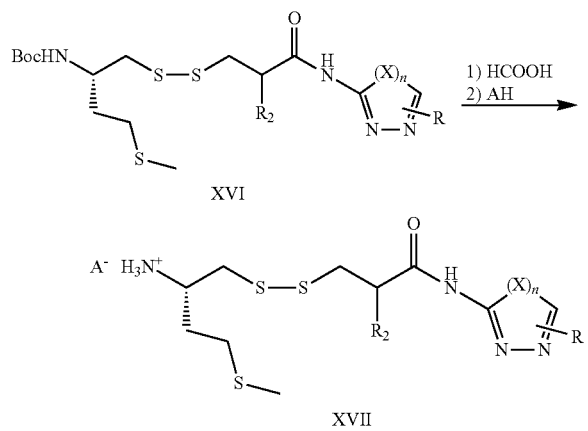

Amino heterocycle XV is synthesized according to methods described in the literature.

For example, 2-amino-5-ethyl-(1,3,4)thiadiazole XVa is obtained as described (Takatori et al., Yakugaku Zasshi 79,1959,913) by condensation of thiosemicarbazide XVIII and propionyl chloride XIX.

2.a.2)

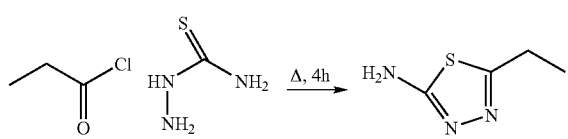

According to an alternative method, compounds of formula (1), wherein radical $R_5$ represents a heterocycle, can be obtained by condensation of heterocycle XV on compound XII, leading to XX. After cutting the disulfide bridge, as previously described, the compound obtained XXI is condensed on II to lead to XVI.

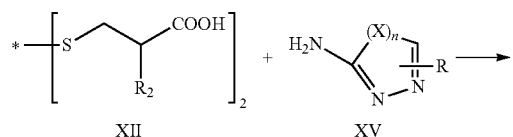

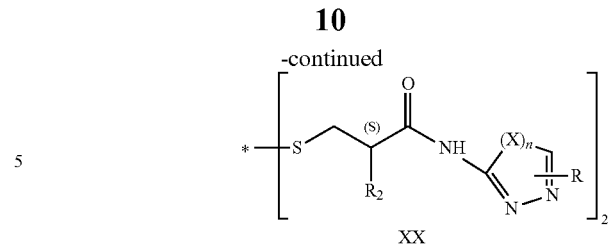

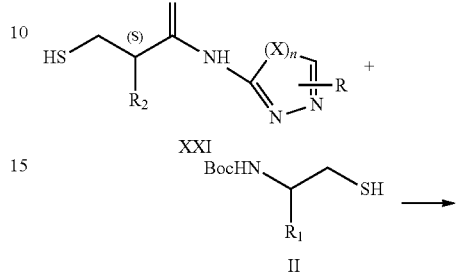

XVI

The invention also has as an object pharmaceutical compositions comprising as active ingredient at least one compound of general formula (I) or a salt of same or salt hydrates of same in combination with one or more pharmaceutically acceptable inert carriers or other vehicles. These compounds exhibit the properties of morphine substances, notably analgesia, including peripheral components (inflammatory, neurogenic), beneficial effects on behavior, notably in the case of depression and/or anxiety, without exhibiting their major disadvantages (tolerance, dependence, respiratory depression, constipation).

Thus, contrary to exogenous opioid agonists that interact with delta receptors, the inventive mixed inhibitors have antidepressant effects without the risk of triggering epileptiform activity or convulsions, and they are fast acting (Baamonde A. et al., 1992, Jutkiewicz E. M. et al., 2005). These compounds can pass the blood-brain barrier. The principal application of the compounds according to the invention is thus in the field of analgesia, antidepressants and anxiolytics.

The inventive pharmaceutical compositions can be, as example, compositions administered by oral, nasal (administration by aerosol), sublingual (administration by perlingual diffusion), rectal, parenteral, intravenous and percutaneous route. Examples of compositions administered by oral route include tablets, gelatin capsules, granules, microspheres, powders and oral solutions or suspensions. Radical $R_5$ confers sufficient hydrophily on the compounds according to the invention, which are thus soluble in water and hydrophilic solvents in the presence of absence of various surfactants. Notably, they are soluble in alcohol/polysorbate/water solvents, notably ethanol/Tween®/water and mannitol/water or with the assistance of cyclodextrins suitable for administration in man, which are frequently used for administration by intravenous route. The compositions according to the invention can thus be administered by intravenous route. They can also be administered by oral or nasal route, notably via an aerosol or by perlingual diffusion or within a suitable galenic preparation (microemulsions). Similarly, these compositions can be used for transdermal administration. These compositions can be used notably as major analgesics, powerful analgesics for inflammatory and neurogenic pain, and as antidepressants.

It is very advantageous that the compositions according to the invention can be administered either in the form of aerosols (microemulsions) by oral or nasal route or by intravenous route. These administration routes thus allow administration of the inventive composition by a non-digestive route. This is particularly advantageous when the composition comprises complementary compounds, which can exhibit undesired effects on the digestive system (notably the intestine), such as, for example, of cannabinoid derivatives. This also increases the cerebral bioavailability of compounds or combinations.

Another object of the invention is the use as a drug of compounds as defined above or obtained by a method as defined above.

Surprisingly, it was also noted that the combination of the novel compounds according to the present invention with cannabinoid derivatives leads to even stronger analgesic effects (superior to the sum of each effect observed for each compound, i.e., for the compounds according to the invention or the cannabinoid derivatives).

Until 1954, cannabis was regarded as a medicinal plant exhibiting multiple properties: analgesic, antispasmodic, anticonvulsive, anti-inflammatory, anti-vomitive, bronchodilator, vasodilator, relaxant and soporific. Recently, anti-proliferative and anti-neurodegenerative properties have been demonstrated.

Several harmful effects of cannabis, generally related to overdose, have been described: anxiety attacks for depressed patients and hallucinations when the product is consumed in drinks (tea) or food (cakes).

The effects of cannabis are explained by its action on cannabinoid receptors. These receptors are present in many cerebral structures and an endogenous molecule naturally related to it, anandamide, has been identified.

Two types of receptors have been characterized: CB1 receptors found in both the central nervous system and the periphery and CB2 receptors which are primarily peripheral. CB1 receptors appear involved in modulating neuronal release of excitory or inhibitory neurotransmitters in the brain. The role of CB2 receptors is less clear, but it seems that they intervene in the modulation of the immune system.

The endogenous molecules related to CB1 and CB2 receptors, called "endocannabinoids," such as anandamide, interact with cannabinoid receptors in the brain and in the periphery by inducing various pharmacologic effects.

The most abundant psychotropic compound present in cannabis (Cannabis sativa) is $\Delta^9$ tetrahydrocannabinol ($\Delta^9$ THC).

$\Delta^9$ THC induces numerous pharmacological responses, such as analgesia, hypothermia, reduced locomotor activity and a loss of alertness and attention due to interactions with brain CB1 receptors. Some of these properties have advantageous therapeutic applications for the treatment of pain and glaucoma, as well as to attenuate nausea and to stimulate the appetite of patients treated with antitumor and antiviral compounds that have severe side effects. $\Delta^9$ THC, and more generally CB1 receptor agonists, is also able to reduce painful effects associated with multiple sclerosis while reducing the progress of the disease. Nevertheless, this led to the development of SATIVEX, which is a preparation directly arising from the plant (Cannabis sativa) and which contains a mixture in equal parts of $\Delta^9$ THC and cannabidiol (another substance present in the plant). This preparation is currently at the end of clinical testing. However, the doses administered by orobuccal route are high and side effects have been observed (Current Opinion in Investigational Drugs 2004, 5, 748).

Another characteristic of the endogenous endocannabinoid (anandamide) system relates to the mode of synthesis and secretion of this specific neurotransmitter. Formed by enzymatic route from organelle membrane phospholipids, anandamide is secreted by a transporter from a post-synaptic neuron to interact with CB1 receptors located on a presynaptic terminal (retrograde neurotransmission) (Piomelli et al., TIS, 2000, 21, 218-224).

However, several behavioral effects, such as a loss of alertness and attention, sedation, ataxia, vision trouble, tachycardia, hypothermia and behavioral disturbances such as hallucinations, anxiety, panic attacks and memory problems, produced by chronic exposure to natural or synthetic cannabinoids, limit their clinical use (reviewed in E. A. Carlini, The good and the bad effects of (–)-trans-delta-9-tetrahydrocannabinol $\Delta^9$THC on humans, Toxicon, 2004, 44, 461-467). Moreover, in man, the analgesic effects of $\Delta^9$ THC are obtained at high doses near to the amounts that cause the adverse effects mentioned above (Campbell F. A. et al., Are cannabinoids an effective and safe treatment option in management of pain? A quantitative systemic review, Br. Med. J., 2001, 323, 12-16).

Surprisingly, it has been noted that the co-administration (simultaneous or over time) of low doses of cannabinoid derivatives (notably $\Delta^9$ THC) potentiates the analgesic effect and the antidepressant effect of the derivatives according to the invention (formula (I)) without significantly inducing harmful effects of said cannabinoids, which by IV route appear beginning at 4-5 mg/kg (sedation).

In the present invention, the expression "very low cannabinoid concentrations" means cannabinoid concentrations below those inducing said undesirable side effects.

In the present invention, the expression "cannabinoid" means $\Delta^9$ THC, synthetic CB1 receptor agonists or anandamide degradation inhibitors. The cannabinoids introduced into the compositions according to the invention are preferably $\Delta^9$ THC.

The invention also has as an object a pharmaceutical composition comprising at least one compound of formula (I) as defined above, at least one cannabinoid derivative, notably $\Delta^9$ THC, or a protector of its metabolism (reviewed in Piomelli et al., TIPS, 2000), and a pharmaceutically suitable excipient, in particular an excipient suitable for administration by oral, nasal, intravenous or transcutaneous route.

The invention also relates to the use of at least one cannabinoid derivative, in particular $\Delta^9$ THC, in a pharmaceutical composition to potentiate the analgesic and/or antidepressant effect of compounds of formula (I) as defined above.

The invention also relates to the use of a combination of at least one compound of formula (I) as defined above and of at least one cannabinoid derivative, in particular $\Delta^9$ THC, for preparing a drug intended for the treatment of depression and of pain.

Another object of the invention is a pharmaceutical composition comprising:
i) at least one compound of formula (I) as defined above,
ii) at least one cannabinoid derivative as combination products for simultaneous, separate or staggered use.

Similarly, the invention also has as an object the use of a pharmaceutical composition comprising
i) at least one compound of formula (I) as defined above,
ii) at least one cannabinoid derivative as combination products for simultaneous, separate or staggered use, for manufacture of a drug to treat depression and pain.

Within the framework of the present invention, the term "pain" means the various types of pain, such as acute pain, inflammatory pain and neurogenic pain, including pain associated with multiple sclerosis. The compounds according to the invention, optionally in combination with a cannabinoid derivative, are also suitable for the treatment of glaucoma.

The invention also has as an object the combination of the novel compounds according to the invention with morphine or a derivative of same. Indeed, morphine is also able to potentiate the analgesic effect induced by the compounds according to the invention.

Thus, the invention has as an object a pharmaceutical composition comprising at least one compound of formula (I) as defined above, of morphine or a derivative of same and a pharmaceutically suitable excipient, notably an excipient suitable for administration by oral, nasal, intravenous or transcutaneous route. The composition can in addition comprise at least one cannabinoid derivative, notably $\Delta^9$ THC, or a protector of its metabolism.

The invention also relates to a pharmaceutical composition comprising at least one compound of formula (I) as defined above and in addition Gaba derivatives. The Gaba derivative is preferably Gabapentin or pregabalin. The addition of a Gaba derivative, as demonstrated with Gabapentin, can potentiate the effects induced by the compounds of formula (I). The inventors surprisingly show that Gaba derivatives (in particular Gabapentin) and compounds of formula (I) have synergistic analgesic effects. In particular, administering the two drugs (i.e. a—the compound of formula (I) and b—the Gaba derivative) at a dose (the dose is the weight of drug administered par kilo of the subject to be treated, it is expressed by mg/kg), at which each drug alone does not show analgesic effect, surprisingly was effective. The analgesic effects induced by both drugs are strongly potentiated in such a way that doses of both drugs ineffective if administered alone are effective when associated.

The dose ratio of compound of formula (I): Gaba derivative (Gabapentin) is preferably between 1:2 and 2:1. In particular, the dose ratio of compound of formula (I): Gaba derivative (Gabapentin) is 2:1.

Thus, the invention has as an object a method for treating depression and particularly pain comprising the administration of an effective amount of a synergistic combination of at least one compound of formula (I) as defined above and a Gaba derivative, preferably Gabapentin or pregabalin, to a patient in need thereof.

This composition can be used as a drug, notably in the treatment of depression and pain. The various compounds can be used as combination products in a simultaneous, separate or staggered fashion.

It is the good aqueous solubility of the compounds according to the invention of formula I that greatly facilitates the constitution of the preparation (microemulsions, in solution in the presence of surfactants, etc.) suitable for therapeutic use by intravenous, nasal, pulmonary (aerosol) or transcutaneous routes.

The effective dose of the inventive compound varies according to a number of parameters, such as, for example, the administration route chosen; the patient's weight, age and sex; the stage of the pathology to be treated; and the patient's sensitivity. Consequently, optimal dosing will be determined, according to the parameters considered to be relevant, by the relevant specialist.

DETAILED DESCRIPTION

The invention will be further illustrated, without being limiting in any way, in the examples below. The list of compounds prepared according to example 12 is given in table 1. For all of the compounds divulged in these examples:

$R_1$ represents the —$CH_2$—$CH_2$—S—$CH_3$ radical,
$CH_2$—(C:CH.S.CH:CH) represents the thiophen-3-ylmethyl radical,
C:CH.CH:CH—CH:CH represents the phenyl radical,
$C_6H_{11}$ represents the cyclohexyl radical.

TABLE 1 radicals for examples 12a-12r.

| Example | $R_2$ | $R_3$ | $R_4$ |
|---------|-------|-------|-------|
| 12a | —$CH_2$—(C:CH•S•CH:CH) | —$CH_3$ | —$CH_2$—C(OCOCH$_3$)(CH$_2$OCOCH$_3$) |
| 12b | —$CH_2$—(C:CH•S•CH:CH) | —$CH_3$ | —$CH_2$—$CH_2$—$SO_2$—$CH_3$ |
| 12c | —$CH_2$—(C:CH•S•CH:CH) | —$CH_3$ | —CH(CH$_3$)—O—CO—O—$C_2H_5$ |
| 12d | —$CH_2$—(C:CH•S•CH:CH) | —$CH_3$ | —$CH_2$—CO—O—$C_2H_5$ |
| 12e | —$CH_2$—(C:CH•S•CH:CH) | —CH(OH)CH$_3$ | —CH(CH$_3$)—O—CO—O—$C_2H_5$ |
| 12f | —$CH_2$—(C:CH•S•CH:CH) | —$CH_3$ | —CH(CH$_2$OCOCH$_3$)$_2$ |
| 12g | —$CH_2$—(C:CH•S•CH:CH) | —$CH_3$ | —CH(CH$_2$OH)$_2$ |
| 12h | —$CH_2$—(C:CH•S•CH:CH) | —$CH_3$ | —H$_2$C—(tetrahydropyran with OH groups) |
| 12i | —C:CH•CH:CH—CH:CH | —CH(OH)CH$_3$ | —CH(CH$_3$)—O—CO—O—$C_2H_5$ |
| 12j | —C:CH•CH:CH—CH:CH | —CH(OH)CH$_3$ | —CH(CH$_2$OCOCH$_3$)$_2$ |
| 12k | —C:CH•CH:CH—CH:CH | —H | —CH(CH$_3$)—O—CO—O—$C_2H_5$ |
| 12l | —C:CH•CH:CH—CH:CH | —H | —CH(CH(CH$_3$)$_2$)—O—CO—O—$C_2H_5$ |
| 12m | —C:CH•CH:CH—CH:CH | —H | —CH($C_6H_{11}$)—O—CO—O—$C_2H_5$ |
| 12n | —C:CH•CH:CH—CH:CH | —H | —CH(C:CH•CH:CH—CH:CH)—O—CO—O—$C_2H_5$ |
| 12o | —C:CH•CH:CH—CH:CH | —H | —CH(CH$_3$)—O—CO—$C_2H_5$ |
| 12p | —C:CH•CH:CH—CH:CH | —H | —CH(CH(CH$_3$)$_2$)—O—CO—$C_2H_5$ |
| 12q | —C:CH•CH:CH—CH:CH | —H | —CH($C_6H_{11}$)—O—CO—$C_2H_5$ |
| 12r | —C:CH•CH:CH—CH:CH | —H | —CH(C:CH•CH:CH—CH:CH)—O—CO—$C_2H_5$ |

FIGURE CAPTIONS

FIG. 1: Dose/response curve of analgesia induced by morphine or compound 15 injected by IV route in mice (hot plate test, 52° C.); X-axis: dose in mg/kg, Y-axis % analgesia.

The black (upper) line corresponds to the results obtained for morphine, the grey (lower) line corresponds to the results obtained for compound 15.

FIG. 2:

A) Antinociceptive response induced by compound 15 injected per os 20 min before the hot plate test (52° C., jump latency, seconds) in male OF1 mice (n=10); X-axis: dose of compound 15 in mg/kg, Y-axis % analgesia.

B) Effect kinetics of compound 15 after administration par os (n=10-17); X-axis: time (minutes), Y-axis % analgesia.

Figure 3:
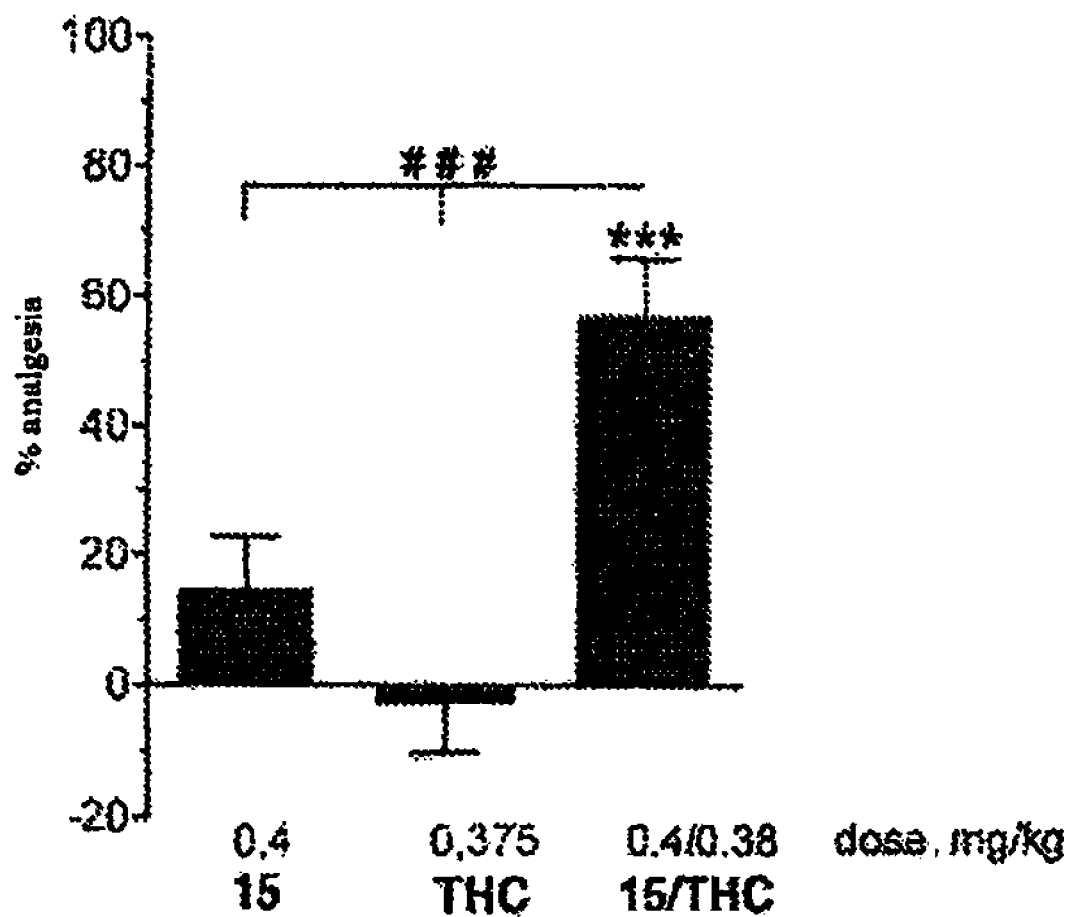

FIG. 3: Antinociceptive response induced by the combination of compound 15 and $\Delta^9$-tetrahydrocannabinol. Hot plate (52±1° C.), jump latency, male OF1 mice. Cuff-off: 240 sec. * * * p<0.001 versus control, ### p<0.001 versus compound 15 and $\Delta^9$-THC. ANOVA+Newman-Keuls.

X-axis: doses of compound 15 (0.4 mg/kg), THC (0.375 mg/kg) and compounds 15/THC (0.4 and 0.38 mg/kg), Y-axis: % analgesia.

FIG. 4.

A) Time course of the inhibition induced by compound 15 (25 mg/kg; p.o.) on osteosarcoma-induced thermal hyperalgesia measured in the unilateral hot plate test in mice.

X-axis: time (minutes), Y-axis: thermal latencies (seconds)
● left paws
○ right paws Means and their corresponding S.E.M. are represented. **P<0.01, compared with the contralateral paw measured at the same time, Student's t test. ●●P<0.01, compared with the basal value (time 0) of the same paw, Dunnett's t test.

B) Effect induced by different doses of compound 15 (12.5-50 mg/kg; p.o.) on thermal latencies measured by the unilateral hot plate test in both paws of mice inoculated in their right paw with NCTC 2472 cells.

X-axis: doses of compound 15 (mg/kg), Y-axis: % thermal latencies (seconds)

On the left of the graph: left paws; on the right of the graph: right paws (inoculated)

Means and their corresponding S.E.M. are represented. **P<0.01, compared with solvent-treated paws. Dunnett's t test.

Figure 5:
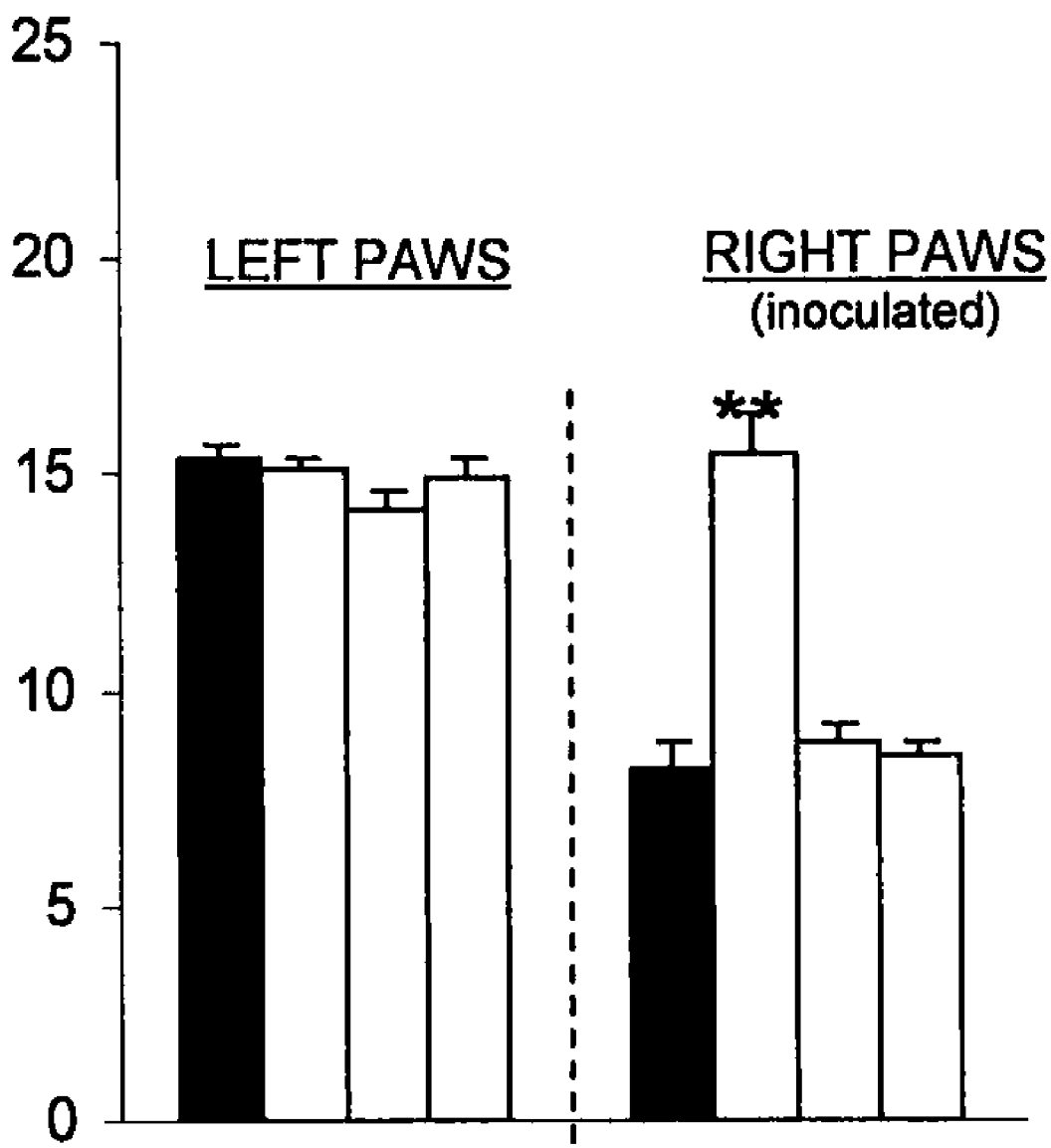

FIG. 5: Inhibition induced by 2 mg/kg of naloxone-methiodide (NAL-MET) of the antihyperalgesic effect evoked by 25 mg/kg of compound 15 on osteosarcoma-induced thermal hyperalgesia measured in the unilateral hot plate test in mice X-axis: doses of compound 15 (mg/kg) (above) or of NAL-MET (below), Y-axis: % thermal latencies (seconds)

On the left of the graph: left paws; on the right of the graph: right paws (inoculated)

Means and their corresponding S.E.M. are represented. **P<0.01, compared with solvent-treated paws. Dunnett's t test.

FIG. 6:

A) Time course of the effect of Gabapentin (25 mg/kg; i.p.) on osteosarcoma-induced thermal hyperalgesia measured in the unilateral hot plate test in mice.

X-axis: time (minutes), Y-axis: thermal latencies (seconds)
● left paws
○ right paws Means and their corresponding S.E.M. are represented. **P<0.01, compared with the contralateral paw measured at the same time, Student's t test. ●●P<0.01, compared with the basal value (time 0) of the same paw, Dunnett's t test.

B) Effect induced by different doses of Gabapentin (6.25-25 mg/kg; i.p) on thermal latencies measured in the unilateral hot plate test in both paws of mice inoculated in their right paw with NCTC 2472 cells.

X-axis: doses of Gabapentin (mg/kg), Y-axis: % thermal latencies (seconds)

On the left of the graph: left paws; on the right of the graph: right paws (inoculated)

Means and their corresponding S.E.M. are represented. **P<0.01, compared with solvent-treated paws. Dunnett's t test.

FIG. 7.

A) Lack of effect of the administration of subeffective doses of compound 15 (12.5 mg/kg; p.o.; 20 minutes before testing) or Gabapentin (6.25 mg/kg; i.p.; 60 min before testing) on the osteosarcoma-induced thermal hyperalgesia and antihyperalgesic effect observed when both drugs are administered in combination measured in the unilateral hot plate test in mice 20, 40 and 60 min after the administration of compound 15 (Gabapentin was administered 40 min before compound 15).

X-axis: time (minutes), Y-axis: thermal latencies (seconds)
——— right paws (inoculated)
- - - left paws
○ Solvent +Solvent
Δ Solvent +compound 15 (12.5 mg/kg)
□ Gabapentin (6.25 mg/kg)+Solvent
■ Gabapentin (6.25 mg/kg)+compound 15 (12.5 mg/kg)

Means and their corresponding S.E.M. are represented. **P<0.01, compared with the corresponding solvent-treated paws at every time. Newman-Keuls test.

B) Isobologram showing the interaction between compound 15 (p.o., 20 min before testing) and Gabapentin (i.p., 60 min before testing) in the unilateral hot plate test. Horizontal and vertical bars indicate S.E.M. The oblique line between the x and y axis is the theoretical additive line. The point in the middle of this line is the theoretical additive point calculated from the individual drug ED50 values. The point below the line is the experimental ED50 value obtained with the combination.

X-axis: Gabapentin concentration (mg/kg), Y-axis: compound 15 concentration (mg/kg)

EXAMPLE 1

Synthesis of Boc-methioninethiol (Compound 1)

This compound is prepared following the protocol described in J. Med. Chem., 35, 1992, 2473. White solid: mp: 37° C.; Rf (Cyclohexane (CHex), ethyl acetate (AcOEt)=1.1) 0.73; $\alpha_D^{20°\,C.}$: −21.1° (c=1.0 CHCl$_3$).

EXAMPLE 2

Synthesis of (2S)-2-mercaptomethyl-3-phenyl propanoic acid (Compound 2)

Step 1. 2-acetylthiomethyl-3-phenylpropanoic acid methyl ester, obtained by the action of thioacetic acid on the methyl ester of the corresponding acrylate, prepared according to (Ber., 57, 1924, 1116), is treated with α-chymotrypsin according to the general protocol described in (Bioor. Med. Chem. Let., 3, 1993, 2681).

Yield: 71.4%; enantiomeric excess (ee): 88%, $\alpha_D^{20°\,C.}$: −42.70°.

Step 2. (2S)-mercaptomethyl-3-phenylpropanoic acid. The compound of step 1 is dissolved in 0° C. degassed methanol (MeOH). Under inert atmosphere, 3 equivalents (eq) of 1 N soda (NaOH) are added. The mixture is agitated 30 min at room temperature (RT). The mixture is acidified by adding 6 N hydrochloric acid (HCl) (25 ml) and MeOH is evaporated under reduced pressure. The aqueous phase is extracted by 2×125 ml AcOEt. The organic phase is washed by a solution of saturated sodium chloride (sat. NaCl) then dried on sodium sulfate ($Na_2SO_4$) and evaporated to dryness. A yellow oil is obtained.

Yield 100%. Kromasil C18 HPLC $CH_3CN/H_2O$ (0.5% trifluoroacetate TFA) 60-40 4.96 min.

EXAMPLE 3

Synthesis of (2RS)2-mercaptomethyl-3-thiophen-3-ylpropanoic acid (Compound 3)

Step 1: A mixture of dimethylmalonate (392 mmol, 45 ml, 1 eq), thiophen-3-yl aldehyde (0.357 mmol), piperidine (1.87 ml; 0.05 eq) and benzoic acid (4.58 g; 0.05 eq) is refluxed 12 h, using a Dean-Stark apparatus, in 270 ml of toluene. The organic phase is washed with 2×140 ml of 1 N HCl, 2×140 ml 10% sodium carbonate ($NaHCO_3$) and 140 ml of saturated NaCl. The organic phase is dried on $Na_2SO_4$ and evaporated to dryness. An oil is obtained.

Yield 100%. Kromasil C18 HPLC $CH_3CN/H_2O$ (0.5% TFA) 60-40: 5.97 min.

Step 2: The compound of step 1 (340 mmol) is solubilized in MeOH (540 ml).

The mixture is cooled to 0° C. and sodium borohydride ($NaBH_4$) is added little by little. The mixture is agitated 15 min at room temperature. The reaction is quenched by adding 450 ml 1 N HCl. Methanol is evaporated and the reaction mixture is extracted with 2×500 ml of chloroform ($CHCl_3$). The organic phase is washed with sat. NaCl then dried on $Na_2SO_4$ and evaporated to dryness. An oil is obtained.

Weight=64.1 g. Yield 82.4%.

Kromasil C18 HPLC $CH_3CN/H_2O$ (0.5% TFA) 60-40: 5.91 min.

Step 3: The preceding compound (30 mmol) is dissolved in MeOH (27 ml). The mixture is cooled to 0° C. and a solution of potash KOH (1.71 g 30.6 mmol) in MeOH (365 ml) is added little by little. The mixture is agitated 48 h at 4° C. Methanol is evaporated and the solid obtained is triturated in ethyl ether $Et_2O$. The solid obtained is filtered, washed and dried. W=25.2 g. Yield 71.0%.

Kromasil C18 HPLC $CH_3CN/H_2O$ (0.5% TFA) 60-40: 3.79 min.

Step 4: The preceding compound (21.9 mmol) is dissolved in THF (30 ml). Diethylamine $Et_2NH$ (3.0 ml; 2 eq) and 37% formaldehyde (3.7 ml; 1.5 eq) are added. The mixture is refluxed overnight. THF is evaporated and the mixture is taken up in 90 ml AcOEt. The organic phase is washed with 3×30 ml 1 N HCl, sat. NaCl then dried on $Na_2SO_4$ and evaporated to dryness. A colorless oil is obtained.

W=13.1 g. Yield 72.0%.

Kromasil C18 HPLC $CH_3CN/H_2O$ (0.5% TFA) 50-50: 14.75 min.

Step 5: The preceding compound (72 mmol) is brought to 80° C. for 5 h in thioacetic acid $CH_3COSH$ (10 ml, 144 mmol, 2 eq). The thioacetic acid is evaporated under reduced pressure. The mixture is coevaporated several times with cyclohexane. An orange oil is obtained. W=18.6 g. Yield 100%.

Kromasil C18 HPLC $CH_3CN/H_2O$ (0.5% TFA) 50-50: 17.16 min.

Step 6. The compound of step 5 is dissolved in degassed MeOH at 0° C. Under inert atmosphere, 3 eq of 1 N NaOH are added. The mixture is agitated 30 min at RT. The mixture is acidified by adding 6 N HCl (25 ml) and MeOH is evaporated under reduced pressure. The aqueous phase is extracted with 2×125 ml AcOEt. The organic phase is washed with sat. NaCl then dried on $Na_2SO_4$ and evaporated to dryness. A yellow oil is obtained.

Yield 100%. Kromasil C18 HPLC $CH_3CN/H_2O$ (0.5% TFA) 50-50 6.80 min.

EXAMPLE 4

Synthesis of (2S)-2-mercaptomethyl-3-thiophen-3-ylpropanoic acid (Compound 4)

Step 1: 2-acetylthiomethyl-3-thiophen-3-ylpropanoic acid methyl ester, described in step 5 of the synthesis of compound 3, is treated with the α-chymotrypsin, as described in the synthesis of 2 (step 1). Yield 87.3%. Kromasil C18 HPLC $CH_3CN/H_2O$ (0.5% TFA) 50-50 7.37 min. ee=76%

Step 2: (2S) acetylthiomethyl-3-thiophen-3-ylpropanoic acid, obtained in step 1, is treated as described in step 2 of compound 2. Yield 97.0%. Kromasil C18 HPLC $CH_3CN/H_2O$ (0.5% TFA) 50-50 6.80 min.

EXAMPLE 5

Synthesis of 2(2S)-benzyl3((2S)2t-butyloxycarbonylamino-4-methylsulfanyl-butyldisulfanyl)-propanoic acid (Compound 5)

A mixture of 23 ml MeOH and 23 ml THF is cooled to 0° C. under nitrogen and chlorosulfonylchloride (1.3 ml, 15.25 mmol, 1.09 eq) is added. The mixture is agitated 15 min at 0° C. to give methoxy carbonylsulfenyl chloride. Then, compound 1 (14.86 mmol, 1.06 eq) in 16 ml THF/MeOH is added all at once. The mixture is returned to room temperature and agitated 30 min. The preceding solution is added drop by drop to a solution of compound 2 (14.02 mmol, 1 eq) in 100 ml of degassed $CHCl_3$ in the presence of $Et_3N$ (1 eq). The solution is agitated 1 h at room temperature. The solvent is evaporated under reduced pressure. The mixture is taken up in dichloromethane $CH_2Cl_2$. The organic phase is washed: 10% citric acid, sat. NaCl, then dried on $Na_2SO_4$ to give a crude product, which is chromatographed on silica with a cyclohexane (CHex)/AcOEt 8/2 mixture then 6/4 as eluent. W=4, 1 g. Yield: 65.9%. Kromasil C18 HPLC $CH_3CN/H_2O$ (0.5% TFA) 70-30: 8.20 min.

EXAMPLE 6

Synthesis of 3-((2S)-2-t-butyloxycarbonylamino-4-methylsulfanyl-butyldisulfanyl)-(2RS)2-thiophen-3-ylmethyl-propanoic acid (Compound 6)

Following the protocol described for the synthesis of 5 and by replacing compound 2 by compound 3, compound 6 is obtained. Yield: 77.0%. Kromasil C18 HPLC $CH_3CN/H_2O$ (0.5% TFA) 70-30: 7.36 min.

EXAMPLE 7

Synthesis of 3-((2S)-2-t-butyloxycarbonylamino-4-methylsulfanyl-butyldisulfanyl)-(2S)-2-thiophen-3-ylmethyl-propanoic acid (Compound 7)

Following the protocol described for the synthesis of 5 and by replacing compound 2 by compound 4, compound 7 is obtained. Yield: 77%. Kromasil C18 HPLC $CH_3CN/H_2O$ (0.5% TFA) 70/30: 7.36 min.

EXAMPLE 8

Synthesis of Alanine Esters

Compound 8a: 2-methyl sulfonylethyl alanine ester, TFA

A solution of 1 eq of BocAlaOH, HOBt (1.2 eq, 879 mg), EDCI (1.2 eq, 1.93 g), $Et_3N$ (triethylamine) (3 eq, 2.9 ml) in 10 ml $CH_2Cl_2$ is agitated 12 h at room temperature in the presence of 1.2 eq of 2-methylsulfonylethanol in solution in $CH_2Cl_2$. The solvent is evaporated under reduced pressure. The reaction mixture is taken up in $AcOEt/H_2O$. The organic phase is washed with 10% citric acid (2×15 ml), 10% $NaHCO_3$ (2×15 ml), saturated NaCl, dried on $Na_2SO_4$ and evaporated under reduced pressure to give a crude product which is chromatographed on silica with a CHex/AcOEt 8/2 mixture as eluent to give 989 mg of product.

Yield: 61.8%. Rf (CHex/AcOEt: 6/4): 0.49.

435 mg (1.488 mmol) of this product are cold solubilized in 2.5 ml of $CH_2Cl_2$ and 1.2 ml of TFA are added. The mixture is agitated 2 h at room temperature. The solvents are evaporated under reduced pressure. The mixture is coevaporated with cyclohexane. Product 8a is cold precipitated in $Et_2O$.

Yield: 100%. Rf ($CH_2Cl_2$/MeOH: 9/1): 0.25.

Compound 8b: 2,3-diacetoxypropyl alanine ester

A solution of 1.026 g (5.428 mmol, 1 eq) of BocAlaOH, HOBt (1.2 eq, 879 mg), EDCI (1.2 eq, 1.93 g), $Et_3N$ (3 eq, 2.9 ml) in 10 ml $CH_2Cl_2$ is agitated 12 h at room temperature in the presence of 2,3-diacetoxypropanol (prepared according to Jensen, Topics in Lipid Chemistry, 1972, 3, 1) in $CH_2Cl_2$. The solvent is evaporated under reduced pressure. The reaction mixture is taken up in $AcOEt/H_2O$. The organic phase is washed with 10% citric acid (2×15 ml), 10% $NaHCO_3$ (2×15 ml), saturated NaCl, dried on $Na_2SO_4$ and evaporated under reduced pressure to give 1.62 g of a crude product. The mixture is chromatographed on silica with a CHex/AcOEt 8/2 mixture as eluent to give 1.29 g of product.

Yield: 68.7%. Kromasil C18 HPLC $CH_3CN/H_2O$ (0.5% TFA) 70-30: 4.25 min.

This product is cold solubilized in 6 ml of $CH_2Cl_2$ and 6 ml of TFA are added. The mixture is agitated 2 h at room temperature. The solvents are evaporated under reduced pressure. The mixture is coevaporated with cyclohexane. Product 8b is cold precipitated in $Et_2O$. W=1.33 g. Yield: 100%. Rf (CHex, EtOAc: 6.4): 0.14.

Compound 8c: 1,3-diacetoxy-2-propyl alanine ester, TFA 1.23 g of 1,3-diacetyl-2-propanol (prepared according to Bentley and McCrae, J. Org. Chem., 1971, 35, 2082) (7 mmol, 1.1 eq) is solubilized in 50 ml of $Et_2O$. Then, diethyl azodicarboxylate (DEAD) (1.2 eq, 1.1 ml), BocAlanine (5.83 mmol, 1 eq) are added followed by triphenylphosphine ($PPh_3$) (1.2 eq, 1.83 g) and the mixture is agitated overnight at room temperature. The solvent is evaporated under reduced pressure. The mixture is chromatographed on silica with a Heptane/AcOEt 8/2 mixture as eluent to give 2.14 g of product. Yield: 84.6%. Rf (Hept/AcOEt: 6/4): 0.42.

2.0 g (4.7 mmol) of this product are cold solubilized in 6.5 ml of $CH_2Cl_2$ and 6.5 ml of TFA are added. The mixture is agitated 2 h at room temperature. The solvents are evaporated under reduced pressure. The mixture is coevaporated with cyclohexane and chromatographed on silica with a $CH_2Cl_2$/MeOH/AcOH 9/1/0.5 mixture as eluent to give 1.16 g of compound 8c.

Yield: 65%. Rf ($CH_2Cl_2$/MeOH/AcOH: 9/1/0.5): 0.22.

Compound 8d: 1,3(t-butyl dimethylsilyl)hydroxy-2 propyl alanine ester

Dihydroxyacetone (2 g, 11.10 mmol) is dissolved in 50 ml of dimethyl formamide (DMF), tert-butyl dimethylsilyl chloride (tBuDMSCl) (4.8 eq, 8.03 g) and imidazole (10 eq, 7.56 g) are added and the mixture is agitated 12 h at 20° C. The mixture is evaporated to dryness, taken up in 150 ml AcOEt. The organic phase is washed with water $H_2O$ (2×50 ml), 10% HCl (2×50 ml), saturated NaCl, then dried on $Na_2SO_4$ and evaporated under reduced pressure to give 20.1 g of crude product. The mixture is chromatographed on silica with CHex/AcOEt 8/2 as eluent to give 5.96 g of product. Yield: 84.5%. Rf ($CH_2Cl_2$/MeOH/AcOH: 9/1/0.5): 0.24.

This product (8.82 g, 27.73 mmol) is dissolved in THF (74 ml) and $H_2O$ (4.8 ml). The mixture is cooled to 5° C. and $NaBH_4$ (965 mg, 1 eq) is added little by little. The mixture is agitated 30 min at 5° C. The excess of $NaBH_4$ is destroyed by adding acetic acid (1 ml). The THF is evaporated under reduced pressure and the mixture is taken up in $CHCl_3/H_2O$. The organic phase is washed with $H_2O$ (2×50 ml), sat. $NaHCO_3$ (2×50 ml), saturated NaCl, then dried on $Na_2SO_4$ and evaporated under reduced pressure to give 8.24 g of product. Yield: 93.0%.

2.93 g of this compound (9.07 mmol, 1.1 eq) are solubilized in 60 ml of $Et_2O$. The mixture is agitated at room temperature and DEAD (1.2 eq, 1.56 ml), amino BocAcid (8.25 mmol, 1 eq) are added followed by $PPh_3$ (1.2 eq, 2.59 g). The solvent is evaporated under reduced pressure. The mixture is chromatographed on silica with a CHex/AcOEt 95/5 mixture as eluent to give 4.42 g of product.

Yield: 92.9%. Rf (CHex/AcOEt: 9/1): 0.65.

881 mg (1.79 mmol) of this product is cold solubilized in 3 ml of $CH_2Cl_2$ and 1.36 ml of TFA are added. The mixture is agitated 2 h at room temperature. The solvents are evaporated under reduced pressure. The mixture is coevaporated with cyclohexane. The mixture is cold precipitated in $Et_2O$ to give 920 mg of compound 8d.

Yield: 100%. Rf (CHex/AcOEt: 9/1): 0.1.

Compound 8e: Carbethoxymethyl alanine ester, TFA

BocAlaOH (5 g, 26.4 mmol) and $Et_3N$ (3.7 ml, 1 eq) are dissolved in 40 ml of AcOEt. The mixture is agitated 10 min at room temperature. Ethylbromoacetate (6.62 g, 1.5 eq) is added and the mixture is refluxed for 30 min. The precipitate is filtered and then 30 ml $H_2O$ and 50 ml AcOEt are added to the filtrate. The aqueous phase is extracted with 3×30 ml AcOEt. The organic phase is washed with 10% citric acid (2×30 ml), 10% $NaHCO_3$ (2×30 ml), saturated NaCl, then dried on $Na_2SO_4$ and evaporated under reduced pressure to give 7.09 g of a crude product. The mixture is chromatographed on silica with a CHex/AcOEt 6/4 mixture as eluent to give 4.68 g of product.

Yield: 64.3%. Rf (CHex/AcOEt: 6.4): 0.35.

500 mg (1.81 mmol) of this product is cold solubilized in 3 ml of $CH_2Cl_2$ and 1.4 ml of TFA are added. The mixture is agitated 2 h at room temperature. The solvents are evaporated under reduced pressure. The mixture is coevaporated with cyclohexane. Product 8e is cold precipitated in $Et_2O$.

W=525 mg. Yield: 100%. Rf ($CH_2Cl_2$/MeOH: 95/5): 0.14.

Compound 8f: Ethylcarbonate-1-ethyl alanine ester, TFA

Boc Ala (76.54 mmol) and $Et_3N$ (12.27 ml, 1.2 eq) are dissolved in 70 ml of AcOEt. The mixture is agitated 15 min at room temperature. Ethyl-1-chloroethylcarbonate (prepared according to Barcelo et al., Synthesis, 1986, 627) (14.01 g, 1.2 eq) and sodium iodine NaI (926 mg, 0.1 eq) are added and the mixture is refluxed for 16 h. The precipitate is filtered and then 200 ml $H_2O$ and 200 ml AcOEt are added to the filtrate. The aqueous phase is extracted with 3×300 ml AcOEt. The organic phase is washed with 10% citric acid (2×150 ml), 10% $NaHCO_3$ (2×150 ml), saturated NaCl, then dried on $Na_2SO_4$ and evaporated under reduced pressure to give 24.5 g of a crude product. The mixture is chromatographed on silica with a CHex/AcOEt 9/1 mixture as eluent to give 18.1 g of product.

Yield: 77.51%. Rf ($CH_2Cl_2$/MeOH: 9/1): 0.33.

9.15 g (30 mmol) of this product are cold solubilized in 23 ml of $CH_2Cl_2$ and 23 ml of TFA are added. The mixture is agitated 2 h at room temperature. The solvents are evaporated under reduced pressure. The mixture is coevaporated with cyclohexane. Product 8f is cold precipitated in $Et_2O$.

W=9.57 g. Yield: 77.5% (2 steps). Rf (CHex/AcOEt: 6/4): 0.1.

Compound 8g: Glucosyl alanine ester, TFA

Pentachlorophenol (3 eq, 10 g, 37.54 mmol) is solubilized at 0° C. in 12 ml AcOEt and N,N'-dicyclohexylcarbodiimide (DCC) (2.58 g, 12.51 mmol) is added. The mixture is left 12 h at −20° C. Cold hexane (10 ml) is added to the mixture and the solid is filtered and washed with cold hexane. The solid is recrystallized in hexane to give 10.3 g of brown solid. Yield: 82.0%. Mp: 115-130° C.

This complex is added to 120 ml of AcOEt. After total dissolution, BocAlanine (1.0 eq, 10.25 mmol) is added and the mixture is agitated overnight at room temperature. The solvent is evaporated under reduced pressure and then 100 ml of $Et_2O$ are added. The suspension is cooled for 1 h and then the solid is filtered. The latter is suspended in 100 ml dioxane, filtered and washed with 2×20 ml dioxane. The filtrate is evaporated to dryness. The residue is treated again by dioxane to eliminate dicyclohexylurea (DCU). It is then suspended in 100 ml $Et_2O$ and placed in the freezer overnight. The solid is filtered and then dried to give 1.29 g of brown solid. Yield: 27.8%.

To a solution of glucose (3 eq, 1.54 g) in 57 ml of redistilled pyridine is added the preceding compound and imidazole. The mixture is agitated overnight at room temperature. The solvent is evaporated under reduced pressure to give a crude product. The mixture is chromatographed on silica with a AcOEt/AcOH 20/1 mixture as eluent to give 883 mg of product. Yield: 88.3%. Rf (AcOEt/AcOH: 20/1): 0.13.

883 mg (2.51 mmol) of this product are cooled to 0° C. and 61 ml of TFA are added. The mixture is agitated 5 min at 0° C. and then 30 min at room temperature. The TFA is evaporated under reduced pressure. The mixture is coevaporated with cyclohexane. The mixture is cold precipitated in $Et_2O$ to give 746 mg of brown compound 8g.

Yield: 81.3%. Rf (AcOEt/AcOH: 10/1): 0.10.

EXAMPLE 9

Synthesis of Threonine Esters

Compound 9a: 1,3-diacetyl-2-propyl threonine ester, TFA

This compound is obtained following the protocol described for 8c, replacing Boc-alanine by Boc-threonine.

Compound 9b: Threonine ethylcarbonate-1-ethyl ester, TFA

This compound is obtained following the protocol described for compound 8f, replacing Boc-alanine by Boc-threonine.

Yield: 89.7% Rf (CHex/AcOEt: 6/4): 0.1.

EXAMPLE 10

Synthesis of Esters of the Glycine

Compound 10a: ethyl carbonate-1-ethyl glycine ester, TFA

This compound is obtained following the protocol described for compound 8f, replacing Boc-alanine by Boc-glycine.

Yield: 92% Rf (CHex/AcOEt 8/2) 0.22.

Compound 10b: Ethyl carbonate 1-(-2-methyl) propyl glycine ester, TFA

This compound is obtained following the protocol described for compound 10a, replacing ethyl-1-chloroethyl-carbonate by ethyl-1-chloro-2-methyl-propyl carbonate.

Yield: 88% Rf (CHex/AcOEt 8/2) 0.12.

Compound 10c: Ethyl carbonate methylcyclohexyl glycine ester, TFA

This compound is obtained following the protocol described for compound 10a, replacing ethyl-1-chloroethyl carbonate by ethyl-chloromethyl cyclohexyl carbonate.

Yield: 78%; Rf (CHex/AcOEt 7/3) 0.31.

Compound 10d: Ethyl carbonate methylphenyl glycine ester, TFA

This compound is obtained following the protocol described for compound 10a, replacing ethyl-1-chloroethyl carbonate by ethyl chloromethylphenyl carbonate.

Yield: 82%; Rf (CHex/AcOEt 7/3) 0.46.

Compound 10e: 1-(2-amino-acetoxy)-ethyl propionic acid ester (Gly-OCH($CH_3$)O—COEt).

This compound is obtained by condensation between Boc-Gly and 1-chloroethyl propionate (1.1 eq) in the presence of NaI (0.2 eq) and $Et_3N$ (1.2 eq) in ethyl acetate (10 ml/mmol) at reflux overnight. After cooling, the organic phase is washed with water, 10% citric acid, 10% NaHCO$_3$, H$_2$O, sat. NaCl and dried on Na$_2$SO$_4$. After evaporation, an oily product is obtained. Yield: 86%.

The Boc group is deprotected as described in the preceding examples. Solid white product, quantitative yield.

Rf (CHex/AcOEt 6/4) 0.64.

Compound 10f: 1-(2-aminoacetoxy)-2-methyl propyl propionic acid ester (Gly-OCH(CH(CH$_3$)$_2$)O—COEt)

This compound is obtained following the protocol described in example 10e, replacing 1-chloroethyl propionate by 1-chloro-2-methyl propyl propionate. White solid, yield: 78% in two steps. Rf (CHex/AcOEt 6/4) 0.56.

Compound 10g: (2-aminoacetoxy)-cyclohexyl-methyl propionic acid ester (Gly-OCH(CHex)O—COEt)

This compound is obtained following the protocol described in example 10e, replacing 1-chloroethyl propionate by chloromethyl(cyclohexyl)propionate.

White solid. Yield: 72% in two steps. Rf (CHex/AcOEt 6/4) 0.38.

Compound 10h: (2-amino-acetoxy)-phenyl-methyl propionic acid ester (Gly-OCH(Ph)O—COEt)

This compound is obtained following the protocol described in example 10e, replacing 1-chloroethyl propionate by chloromethyl(phenyl)propionate.

White solid. Yield: 75% in two steps. Rf (CHex/AcOEt 6/4) 0.42.

EXAMPLE 11

Synthesis of 2-amino-5-ethyl-(1,3,4)thiadiazole

A mixture of 25 g (0.27 mol) of thiosemicarbazide and 46.6 ml propanoyle chloride (0.54 mol, 2 eq) is agitated at 40° C. for 4 h. The propanoyle chloride excess is then evaporated under a vacuum and the residue is triturated in ether. A solid product is obtained. It contains the expected thiadiazole and an impurity that is eliminated by precipitation in ethanol. White solid, 33.6 g (Yield: 83%) Kromasil C18 HPLC Tr 6.32 min in 30% CH$_3$CN.

EXAMPLE 12

Synthesis of Mixed Inhibitors Wherein R$_5$=CH(R$_3$)COOR$_4$

Disulfide 5, 6 or 7 (0.54 mmol) is solubilized in 4 ml of DMF. To it is added benzotriazole-1-yl-oxy-tris-(dimethylamino)-phosphonium hexafluorophosphate (BOP) (1.2 eq, 1.0 g) and diisopropyl-ethyl-amine (DIEA) (284 µl) and then amino acid ester 8, 9 or 10 (1.3 eq). The mixture is agitated 20 min at room temperature and then the DMF is evaporated under reduced pressure. The product is taken up in AcOEt. The organic phase is washed with H$_2$O, 10% citric acid, 10% NaHCO$_3$, sat. NaCl and dried on Na$_2$SO$_4$. The crude product is purified by chromatographed on silica.

The compound obtained (0.38 mmol) is solubilized in 640 µl CH$_2$Cl$_2$ and 320 µl of TFA is added. The mixture is agitated 1 h at room temperature. The solvent excess is evaporated under reduced pressure. The mixture is coevaporated with cyclohexane. The mixture is purified by semi-preparative HPLC or precipitated in a hexane/Et$_2$O mixture.

Compound 12a: 1-(2-(1-(2,3-diacetoxypropoxycarbonyl)-ethylcarbamoyl)-3-thiophen-3-ylpropyldisulfanylmethyl)-3-methylsulfanylpropyl-ammonium trifluoroacetate (Compound 6 or 7+compound 8b)

W: 176 mg; Yield: 66.9%. Kromasil C18 HPLC CH$_3$CN/H$_2$O (0.5% TFA) 40-60: 9.07 and 10.18 min. ESI: (M+H)$^+$=581. Log Kow=1.31.

Compound 12b: 1-(2-(1-(2-methanesulfonylethoxycarbonyl)-ethylcarbamoyl)-3-thiophen-3-yl-propyldisulfanylmethyl)-3-methylsulfanylpropyl-ammonium trifluoroacetate (Compound 6 or 7+Compound 8a)

W: 200 mg; Yield: 74.1%. Kromasil C18 HPLC CH$_3$CN/H$_2$O (0.5% TFA) 40-60: 5.0 and 5.35 min. ESI: (M+H)$^+$=529. Log Kow=−0.13.

Compound 12c: 1-(2-(1-(1-ethoxycarbonyloxyethoxycarbonyl))-ethylcarbamoyl)-3-thiophen-3-ylpropyldisulfanylmethyl)-3-methylsulfanylpropyl-ammonium trifluoroacetate (Compound 6 or 7+Compound 8f)

W: 232 mg; Yield: 71.3%. Kromasil C18 HPLC CH$_3$CN/H$_2$O (0.5% TFA) 50-50: 3.84 and 4.03 min. ESI: (M+H)$^+$=509. Log Kow=1.63.

Compound 12d: 1-(2-(1-ethoxycarbonylmethyloxycarbonylethylcarbamoyl)-3-thiophen-3-yl-propyldisulfanylmethyl)-3-methylsulfanylpropyl-ammonium trifluoroacetate (Compound 6 or 7+Compound 8e)

W: 261 mg; Yield: 83.9%. Kromasil C18 HPLC CH$_3$CN/H$_2$O (0.5% TFA) 50-50: 4.90 and 5.18 min. ESI: (M+H)$^+$=539. Log Kow=1.35.

Compound 12e: 1-(2-(1-(1-ethoxycarbonyloxyethoxycarbonyl)-2-hydroxypropylcarbamoyl)-3-thiophen-3-ylpropyldisulfanylmethyl)-3-methylsulfanylpropyl-ammonium trifluoroacetate (Compound 6 or 7+Compound 9b)

W: 285 mg; Yield: 47.8%. Kromasil C18 HPLC CH$_3$CN/H$_2$O (0.5% TFA) 40-60: 10.55 and 11.09 min. ESI: (M+H)$^+$=594. Log Kow=0.76.

Compound 12f: 1-(2-(1-(2-acetoxy-1-acetoxymethylethoxycarbonyl)-ethylcarbamoyl)-3-thiophen-3-ylpropyldisulfanylmethyl)-3-methylsulfanylpropyl-ammonium trifluoroacetate (Compound 6 or 7+Compound 8c)

W: 171 mg; Yield: 70.1%. Kromasil C18 HPLC CH$_3$CN/H$_2$O (0.5% TFA) 40-60: 7.35 and 8.09 min. ESI: (M+H)$^+$=581. Log Kow=1.31.

Compound 12g: 1-(2-(1-(2-hydroxy-1-hydroxymethylethoxycarbonyl)-ethylcarbamoyl)-3-thiophen-3-ylpropyldisulfanylmethyl)-3-methylsulfanylpropyl-ammonium trifluoroacetate (Compound 6 or 7+Compound 8d)

W: 166 mg; Yield: 67.2%. Kromasil C18 HPLC CH$_3$CN/H$_2$O (0.5% TFA) 40-60: 2.94 and 3.27 min. ESI: (M+H)$^+$=497. Log Kow=−0.29.

Compound 12h: 1-(2-(1-(3,4,5,6-tetrahydroxytetrahydropyran-2-ylmethoxycarbonyl)ethylcarbamoyl)-3-thiophen-3-yl-propyldisulfanylmethyl)-3-methylsulfanylpropyl-ammonium trifluoroacetate (Compound 6 or 7+Compound 8g)

W: 85 mg; Yield: 93.2%. Kromasil C18 HPLC CH$_3$CN/H$_2$O (0.5% TFA) 50-50: 2.34 min. ESI: (M+H)$^+$=585. Log Kow=−1.15.

Compound 12i: 1-(2-((1-(1-ethoxycarbonyloxy-ethoxycarbonyl)-2-hydroxypropylcarbamoyl)-3-phenylpropyldisulfanylmethyl)-3-methylsulfanylpropyl-ammonium trifluoroacetate (Compound 5+Compound 9b)

W: 1.88 g; Yield: 83.8%. Kromasil C18 HPLC CH$_3$CN/H$_2$O (0.5% TFA) 45-55: 7.0 min. ESI: (M+H)$^+$=563. Log Kow=0.76.

Compound 12j: 1-(2-(1-(2-acetoxy-1-acetoxymethylthoxycarbonyl)-2-hydroxypropylcarbamoyl)-3-phenylpropyldisulfanylmethyl)-3-methylsulfanylpropyl-ammonium trifluoroacetate (Compound 5+Compound 9a)

W: 532 mg; Yield: 53.6%. Kromasil C18 HPLC CH$_3$CN/H$_2$O (0.5% TFA) 40-60: 6.16 min. ESI: (M+H)$^+$=605. Log Kow=0.44.

Compound 12k: 1-(2-(1-ethoxycarbonyloxy-ethoxycarbonylmethyl)-carbamoyl)-3-phenyl-propyldisulfanylmethyl)-3-methylsulfanylpropyl-ammonium trifluoroacetate (Compound 5+Compound 10a)

W: 1.76 g; Yield: 89.5%. Kromasil C18 HPLC CH$_3$CN/H$_2$O (0.5% TFA) 50-50: 5.33 min. ESI: (M+H)$^+$=519. Log Kow=1.39.

Compound 12l: 1-(2-((1-ethoxycarbonyloxy-2-methyl-propoxycarbonylmethyl)-carbamoyl)-3-phenylpropyldisulfanylmethyl)-3-methylsulfanyl-propyl-ammonium trifluoroacetate (Compound 5+Compound 10b)

W: 1.2 g; Yield: 82.3%. Kromasil C18 HPLC CH$_3$CN/H$_2$O (0.5% TFA) 50/50 9.33 min, ESI: (M+H)$^+$=547.

Compound 12m: 1-2-((cyclohexyl-thoxycarbonyloxy-methoxycarbonylmethyl)-carbamoyl)-3-phenyl-propyldisulfanylmethyl)-3-methylsulfanyl-propyl-ammonium trifluoroacetate (Compound 5+Compound 10c)

W: 2.1 g; Yield: 65.3%. Kromasil C18 HPLC CH$_3$CN/H$_2$O (0.5% TFA) 50/50 12.65 min, ESI: (M+H)$^+$=587.

Compound 12n: 1-(2-((ethoxycarbonyloxy-phenylmethoxycarbonylmethyl)-carbamoyl)-3-phenyl-propyldisulfanylmethyl)-3-methylsulfanyl-propyl-ammonium trifluoroacetate (Compound 5+Compound 10d)

W: 0.95 g; Yield: 68.1%. Kromasil C18 HPLC CH$_3$CN/H$_2$O (0.5% TFA) 50/50 10.86 min. ESI (M+H)$^+$=581.

Compound 12o: 3-methylsulfanyl-1-(3-phenyl-2-((1-propionyloxy-ethoxycarbonylmethyl)-carbamoyl)-propyldisulfanylmethyl)-propyl-ammonium trifluoroacetate (Compound 5+Compound 10e)

W: 1.6 g; Yield: 81.2%. Kromasil C18 HPLC CH$_3$CN/H$_2$O (0.5% TFA) 50/50 6.82 min. ESI (M+H)$^+$=502.

Compound 12p: 1-(2-((2-methyl-1-propionyloxy-propoxycarbonylmethyl)-carbamoyl)-3-phenyl-propyldisulfanylmethyl)-3-methylsulfanyl-propyl-ammonium trifluoroacetate (Compound 5+Compound 10f)

W: 1.05 g, yield: 83%. Kromasil C18 HPLC CH$_3$CN/H$_2$O (0.5% TFA) 50/50 8.17 min. ESI (M+H)$^+$=531.

Compound 12q: 1-(2-((cyclohexyl-propionylaxy-methoxycarbonylmethyl)-carbamoyl)-3-phenyl-propyldisulfanylmethyl)-3-methylsulfanyl-propyl-ammonium trifluoroacetate (Compound 5+Compound 10g)

W: 1.8 g; Yield: 78.2%. Kromasil C18 HPLC CH$_3$CN/H$_2$O (0.5% TFA) 50/50 12.24 min. ESI (M+H)$^+$=571.

Compound 12r: 3-methylsulfanyl-1-(3-phenyl-2-((phenyl-propionyloxy-methoxycarbonylmethyl)-carbamoyl)-propyldisulfanylmethyl)-propyl-ammonium trifluoroacetate (Compound 5+Compound 10h)

W: 0.98 g; Yield: 76.3%. Kromasil C18 HPLC CH$_3$CN/H$_2$O (0.5% TFA) 50/50 11.25 min. ESI (M+H)$^+$=565.

EXAMPLE 13

Synthesis of Mixed Inhibitors Wherein R$_5$=Heterocycle

Disulfide 5, 6 or 7 (0.54 mmol) is dissolved in 5 ml of CH$_2$Cl$_2$ and the aminothiadiazole of example 11 (1.2 eq), TBTU (O-benzotriazol-1-yl-N,N,N',N'-tetramethyluroniumtetrafluoroborate) (3 eq) and DIEA (diisopropylethylamine) (3 eq) are successively added. The mixture is agitated for 30 minutes at room temperature (approximately 20° C.). The solvent is evaporated under a vacuum and the residue taken up in ethyl acetate. The organic phase is washed with citric acid, water, saturated NaCl and dried on Na$_2$SO$_4$. After vacuum filtration and evaporation, a white solid is obtained.

The compound obtained is dissolved in formic acid and the mixture is agitated 1 h at room temperature. The excess formic acid is evaporated under a vacuum. The residue is taken up ether and gives a white precipitate.

Compound 13a: 3-(2-aminomethylsulfanyl-butyldisulfanyl)-2-benzyl-N-(5-ethyl-(1,3,4)thiadiazol-2-yl)-propionamide W=256 mg (Yield 75%).

EXAMPLE 14

Change of Counter-Ion

The compounds of example 12 and example 13 (1 mmol) are solubilized in 9 ml of distilled AcOEt. The organic phase is washed with 12 ml 0.1 N NaHCO$_3$. The organic phase is then dried and evaporated under reduced pressure. The product is taken up in AcOEt (3 ml), cooled to 0° C. and 1 eq of the chosen AH acid in 3 ml of AcOEt is added. The solvent is evaporated and the product is cold precipitated in an Et₂O/hexane mixture.

(A=phosphate, hydrochloride, acetate, methanesulfonate, borate, lactate, fumarate, succinate, hemisuccinate, citrate, tartrate, hemitartrate, maleate, ascorbate, hemifumarate, hexanoate, heptanoate, hippurate, hydrocinnamate, phenylglyoxylate, nicotinate).

EXAMPLE 15

Pharmacological Results—Compound According to the Invention

Compound 15 of the following formula was tested in the various biological tests below.

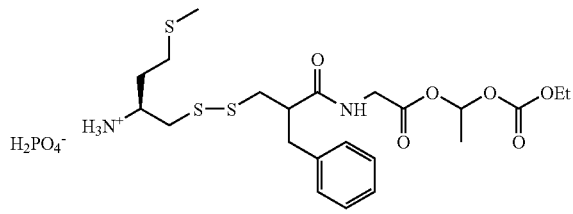

Hot plate test: this test relates to the licking and jumping reflex in mice on a plate heated at 52° C. (measurement of jump latency in the examples given). The results are expressed in % of maximum possible effect (% MPE), i.e., expressed as a percentage of analgesia, using the following equation:

$$\% \, MPE = \frac{(\text{Measured latency time} - \text{control latency time})}{(\text{Maximum latency time} - \text{control latency time})}$$

Maximum latency time=240 seconds.

The results are expressed in term of mean±SEM. The differences observed are considered significant when the values of p are less than 0.05. The test used is an ANOVA test with a multiple comparison test.

a) Antinociceptive responses observed after injection by intravenous (IV) route of compound 15 in the hot plate test (52° C., response per jump) in male mice (n=10).

Compound 15 is dissolved in a water/mannitol mixture (50 mg/ml). Jump latency times are measured 10 min after the injections by intravenous route.

TABLE 2

| Dose mg/kg | % analgesia |
|---|---|
| 10 | 33.4 ± 7.5** |
| 20 | 59.2 ± 9.6*** |
| 40 | 90.2 ± 7.0*** |

The results (table 2) show that compound 15 exhibits a dose-dependant analgesic action.

p<0.01; *p<0.001 versus vehicle.

Effective dose 50, $ED_{50}$, is 16.1 mg/kg.

$ED_{50}$ is the dose (in g/kg of body weight) that gives the desired effect in 50% of the population in which it is tested.

b) Antinociceptive effect of compound 15 (100 mg/kg par os) on vocalization threshold when pressure is applied to the paw of a rat (male Sprague Dawley) with an inflamed paw, inflammation being induced by intraplantar injection of carrageenan.

Compound 15 and a vehicle (ethanol/polyethylene glycol (PEG) 400/water, 10/40/50) are administered 180 min after intraplantar injection of carrageenan (1% in saline solution).

TABLE 3

| | Vocalization threshold (g) |
|---|---|
| Basal threshold | 298.8 ± 18.7 |
| Inflamed paw + vehicle | 205.5 ± 17.8 |
| Inflamed paw + compound 15 | 292.5 ± 20.1*** |

The baseline for vocalization threshold when pressure is applied to the paw is measured before inflammation (B) and for the inflamed paw 20 min after injection of compound 15 or the vehicle. The results are given in table 3 and are expressed as mean±SEM, n=10. The differences observed are considered significant when the values of p are less than 0.05. These results show that compound 15 is effective in the treatment of neurogenic inflammatory pain. ***p<0.001 versus vehicle.

c) Antinociceptive responses observed after IV injection of compound 15 dissolved in ethanol/surfactant/water (10/10/80) in the hot plate test (52° C., response per jump) in male OF1 mice and comparison of the responses according to the nature of the vehicle.

Compound 15 is dissolved in a ethanol/Cremophor® EL/water mixture. Jump latency times are measured 10 min after intravenous injection. The results are given in FIG. 1.

The dose-dependant response provides an analgesic response at an effective dose 50 ($ED_{50}$) of 1.9±0.4 mg/kg. This value is close to that observed with morphine ($ED_{50}$=1.3±0.2 mg/kg). p<0.01 versus vehicle. *p<0.001.

Compound 15 is also soluble in ethanol/Tween®/water solvents, frequently used for administration by intravenous route in man.

In these solvents, the differences are not significantly different from those observed with Cremophor® EL. This is illustrated in table 4 (jump latency time 10 min after injections) at the same concentration of 2.5 mg/kg IV. ***p<0.001 versus vehicle.

TABLE 4

| | % analgesia |
|---|---|
| Cremophor EL | 56.2 ± 6.9*** |
| Tween 80 | 44.7 ± 6.2*** |
| Tween 20 | 48.4 ± 10.2*** | d) Antinociceptive effect of compound 15 injected per os 20 min before the hot plate test: a) dose-response curve; b) effect kinetics after administration per os of 200 m/kg.

Figures 2A, 2B:
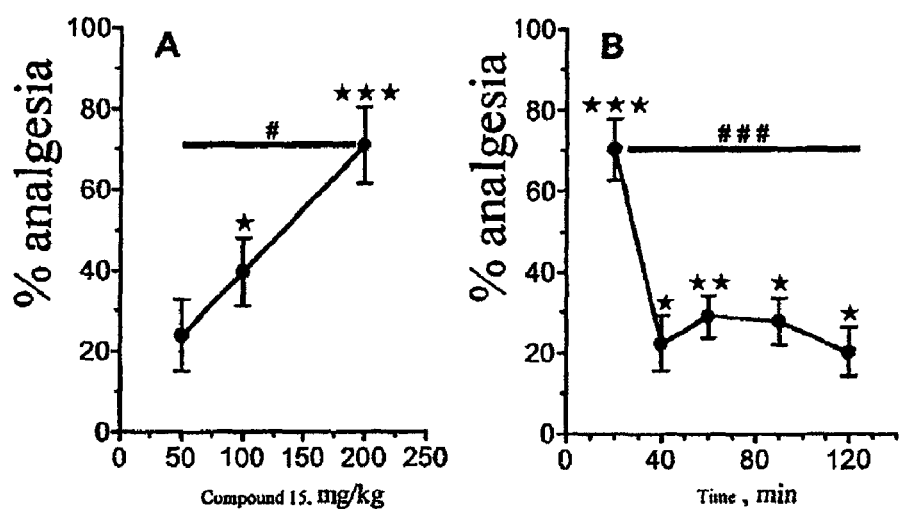

Compound 15 is dissolved in an ethanol/PEG400/water 10/40/50 mixture. The results, given in the FIGS. 2a and 2b, show that compound 15 exhibits a dose-dependant analgesic effect (2a), $ED_{50}$=135 mg/kg, and that the analgesic effect of compound 15 is very high night after administration and persists, with a lesser effect, for at least two hours (2b).

*p<0.05; p<0.01; *p<0.001 versus vehicle.
p<0.05; ###p<0.001 versus compound 15.

e) Comparative antinociceptive responses observed after IV injection of compound 15 (n=14-17) or of compound A (n=8-14), 5 mg/kg, in the hot plate test (52° C., response per jump) in male mice.

Compound A is the compound of formula:

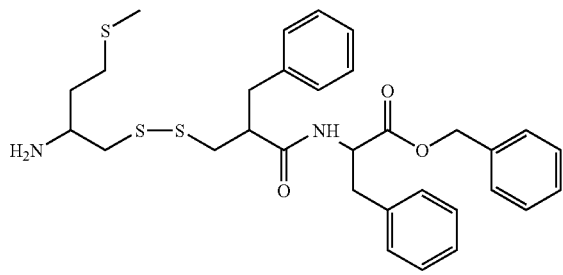

which was described in prior patent application WO 91/02718 (example 7). It is a mixed inhibitor of neprilysin and aminopeptidase that exhibits analgesic properties. It is poorly soluble in aqueous or hydrophilic solvents.

Compounds 15 and A are dissolved in an ethanol/Cremophor EL/water 10/10/80 mixture. Jump latency times are measured 10 min after intravenous injection.

TABLE 5

| | % analgesia |
|---|---|
| Compound 15 | 87.6 ± 4.6**,### |
| Compound A | 51.1 ± 7.6** |

The results given in table 5 show that at identical doses (low for administration of compound A by IV route), compound 15 is more active than compound A.

**p<0.01 versus vehicle, ###p<0.001 versus compound A.

f) Analgesia induced by morphine or compound 15 injected by IV route in mice (hot plate test, 52° C.).

The analgesia produced by morphine or compound 15 in mice (male OF1) in the hot plate test (52° C.) was measured. Morphine in $H_2O$/NaCl, 9/1000) or compound 15 dissolved in the vehicle EtOH/Cremophor El/water (10/10/80) is injected by IV. The results are measured 10 minutes after injection and latency time is 240 seconds (equation given in examples 15 and 17).

The results are presented in table 6 below:

TABLE 6

| Dose (mg/kg) | 1 | 2.5 | 5 |
|---|---|---|---|
| % analgesia compound 15 | 46.4 ± 5.6*** | 56.3 ± 6.9*** | 87.6 ± 4.6*** |
| % analgesia morphine | 45.5 ± 4.5*** | 66 ± 6.0*** | 100*** |

***p < 0.001, ANOVA test

It is noted that compound 15 has analgesic effects comparable with those obtained with morphine. This agrees with the results of another experiment carried out under identical conditions (FIG. 1, example 15c).

EXAMPLE 16

Analgesic Effect of $\Delta^9$ THC Alone

The analgesia produced by $\Delta^9$ THC in mice (male OF1) in the plate hot test (52° C.) was measured. $\Delta^9$ THC, dissolved in the vehicle EtOH/Cremophor EL/water (10/10/80), is injected by IV route. The results are measured 10 minutes after injection and latency time is 240 seconds (equation given in examples 15 and 17).

The results are presented in table 7 below:

TABLE 7

| Dose (mg/kg) | 0.188 | 0.375 | 0.75 | 1.5 |
|---|---|---|---|---|
| % analgesia | 0.4 ± 3.9 | 18.2 ± 6.4 | 41.2 ± 12.7** | 57.2 ± 10.9*** |

**p < 0.01;
***p < 0.001

It is noted that $\Delta^9$ THC produced a dose-dependant analgesic effect. Significant analgesia values are observed for doses of 0.75 mg/kg and 1.5 mg/kg. At lower doses, the percentage of analgesia is not significant.

EXAMPLE 17

Analgesic Effects of the Compound According to the Invention +$\Delta^9$ THC

The experiments described to demonstrate the magnitude of the synergistic action of the compound according to the invention combined with $\Delta^9$ THC were carried out in rodents (rat and mouse) using antinociception tests classically used in the pharmaceutical industry to demonstrate this type of property, namely:

the hot plate test (Eddie and Leimbach, J. Pharmacol. Exp. Ther. 107, 385-389, 1953) in mice,
the tail-flick test in rats (D'Amour and Smith, J. Pharmacol. Exp. Ther. 72, 74-79, 1941)
the Porsolt swim test in mice (Porsolt Arch. Int. Pharmacodyn. 229, 327, 1977).

For the central tests (hot plate, tail-flick), the concentrations:

in cannabinoids ($\Delta^9$ THC) will preferentially be between 0.3 and 0.5 mg/kg,
in the compound according to the invention (compound 15) will preferentially be between 1 and 2 mg/kg.

The relative concentrations are dependant on nociceptive stimulation.

The $\Delta^9$ THC used in the examples below is a commercial product purchased from Sigma-Aldrich (T2386).

The mixed inhibiter used in the following examples is compound 15 described above (example 15).

Preparing Solutions of the Compounds

All of the compounds were solubilized in an ethanol/Cremophor 80/water=10/10/80 mixture.

For the potentiation experiments (synergy), doses of $\Delta^9$ THC and inhibitors were used that, taken separately, do not induce significant responses.

Mode of Administration

The various compounds are administered, in a mixture in the same syringe, by IV route in the tail of the rat or mouse.

Animals

The mice used in these tests are male OF1 mice. The rats used in these tests are male Sprague-Dawley rats.

Pharmacological Tests

Hot plate test:

This test relates to the licking and jumping reflex in mice on a plate heated at 52° C. The results are expressed in % of maximum possible effect (% MPE), i.e., expressed as a percentage of analgesia, using the following equation:

$$\% \ MPE = \frac{\text{(Measured latency time} - \text{control latency time)}}{\text{(Maximum latency time} - \text{control latency time)}}$$

Maximum latency time=240 s.

The results are expressed in terms of mean±SEM. The differences observed are considered significant when the values of p are less than 0.05.

Tail-flick Test:

This test relates to the tail-flick reflex in the rat, stimulated by radiant heat emanating from a source of light focused on a given part of the tail. The results are expressed as in the preceding experiment by the measurement of a percentage of analgesia according to the same equation. The maximum latency time is fixed arbitrarily at 15 seconds.

Swim Test:

This test measures the immobilization time for a mouse placed in a water bath at 21-23° C., from which it cannot escape. Immobilization time reflects a form of depression; the mice no longer struggle to escape the hostile environment. The results are expressed in immobilization time. Maximum immobilization time is 4 min.

For the need of demonstrating the synergy of the combination of compound 15+$\Delta^9$ THC, a dose-response curve for compound 15 alone and $\Delta^9$ THC alone are prepared in the solvent ethanol/Cremophor EL/H$_2$O (1/1/8) because $\Delta^9$ THC can be used only by IV route at high concentrations under these conditions (example 16). The histogram (FIG. 3) of analgesic responses (hot plate) clearly shows the very high potentiation of the analgesic effect of the $\Delta^9$ THC plus compound 15 combination compared to one or the other of the products alone.

a) Antinociceptive response induced by the injection of a mixture of compound 15 and $\Delta^9$ THC by IV route in male OF1 mouse in the hot plate test (FIG. 3).

The mixture of compounds 15 (0.4 mg/kg) and $\Delta^9$ THC (0.375 mg/kg) are injected in the vehicle ethanol/Tween 80/water (10/10/80). The mice weigh 25-30 grams. This solvent mixture is compatible with administration by IV route in man and in animals.

Jump latency is measured 10 minutes after intravenous injection. The results are expressed as percentage analgesia, using the equation defined above, and are presented in FIG. 3.

The difference observed is considered significant for $p \leq 0.05$—One-way ANOVA followed by a multiple comparison test.

***: $p \leq 0.01$ versus control, ###: $p \leq 0.01$ versus the mixture of compounds 15 and $\Delta^9$ THC.

b) Antinociceptive response induced by injection of a mixture of compounds 15 and $\Delta^9$ THC by IV route in the tail-flick test in male Sprague-Dawley rats. The mixture of compounds 15 (5 mg/kg) and $\Delta^9$ THC (0.375 mg/kg) are injected in the vehicle ethanol/Tween 80/water (10/10/80). Tail-flick latency is measured before injection (pretest) and 10 minutes after intravenous injection (test).

Latency time is 15 seconds. The rats weigh 260-300 grams. The results are presented in table 8.

TABLE 8

| Tail-flick test | |
|---|---|
| | % analgesia |
| Vehicle | −3.9 ± 3.3 |
| Compound 15 | −4.2 ± 1.9 |
| $\Delta^9$ THC | 23.3 ± 2.4*** |
| Compound 15 and $\Delta^9$ THC | 39.2 ± 7.7**,***,# |

***p < 0.001 versus vehicle,
**P < 0.001 versus compound 15,
p < 0.05 versus $\Delta^9$ THC.

The difference observed is considered significant for $p \leq 0.05$. Two-way ANOVA followed by a multiple comparison test: *: $p \leq 0.001$, :$p \leq 0.01$ versus vehicle group; #:$p \leq 0.05$ versus $\Delta^9$ THC group; *$p \leq 0.001$, $p \leq 0.01$ versus compound 15 group.

c) Antidepressant response induced by injection of a mixture of compound 15 and $\Delta^9$ THC by IV route in the swim test in male OF1 mice.

The mixture of compounds 15 (5 mg/kg) and $\Delta^9$ THC (0.375 mg/kg) are injected in the vehicle ethanol/Tween 80/water (10/10/80) by intravenous route 10 minutes before the test.

Total immobilization time is measured for 4 minutes.

The results are presented in table 9. The mice weigh approximately 25-30 grams.

The difference observed is considered significant for $p \leq 0.05$. One-way ANOVA followed by a multiple comparison test: ***: $p \leq 0.001$, *:$p \leq 0.05$ versus vehicle group; ###: $p \leq 0.001$ versus compounds 15/$\Delta^9$ THC group; and $\Delta^9$ THC group.

TABLE 9

| Depression/swim test. | |
|---|---|
| | Mobilization |
| Vehicle | 230.7 ± 4.5 |
| Compound 15 | 180 ± 8.4*** |
| $\Delta^9$ THC | 206 ± 6.1 |
| Compound 15/$\Delta^9$ THC | 137.4 ± 8.8***,### |

***p < 0.001 versus control,
p < 0.001 versus $\Delta^9$ THC and compound 15.

CONCLUSION

It is noted that the administration of a low dose of cannabinoid, $\Delta^9$ THC, i.e., at concentrations less than 0.5 mg/kg by IV route in mice, potentiates the antinociceptive or antidepressant responses induced by compound 15.

Under these conditions, synergy is quite clearly demonstrated when the analgesic effects obtained in the hot plate test in mice by comparing the dose-response curves for $\Delta^9$ THC and compound 15 with the effect produced by sub-analgesic doses of these two compounds (FIG. 3).

It can be noted that the amplification factors of the active dose of $\Delta^9$ THC alone/active dose of $\Delta^9$ THC plus compound 15, and conversely, the active dose of compound 15 alone/active dose of compounds 15+$\Delta^9$ THC, are in both cases much greater than 10 and are not easily calculable precisely since the doses used of compound 15 and $\Delta^9$ THC are inactive when these two molecules are used alone at these same doses.

The intensity of the antinociceptive response elicited by the combination of the inventive compound (mixed inhibiter NEP/APN; for example compound 15) and of $\Delta^9$ THC, both substances being administered at very low doses at which they have no activity, indicate the existence of action synergy between endogenous enkephalins (protected by the inventive compound) and $\Delta^9$ THC. This is corroborated by an isobolographic analysis of pharmacological responses.

EXAMPLE 17

Synergy Between the Analgesic Effects of the Compound According to the Invention and Gabapentin on Neuropathic Pain Several reports demonstrate the ability of Gabapentin to induce antinociceptive responses by acting at peripheral level (Carlton S. M. and Zhou S., Pain 76 (1998) 201-207; Todorovic et al., Br. J. Pharmacol. 140 (2003), 255-260). The fact that Gabapentin dose-dependently increases the latencies of the injured paws at low doses without modifying those of the contralateral ones could fit better with a peripheral than with a central site of action.

The comparison and possible facilitation of compound 15 analgesic effect by Gabapentin was investigated on the animal model of bone cancer induced by intraosteal inoculation of NCTC2472 tumor cells (Honoré P. et al., Neuroscience 98 (2000), 585-588 Mendez L. et al. J. Neurosci. Methods 113 (2002), 91-97).

The methods used to measure the analgenisc effects (antihyperalgesia and allodynia) of various compounds of this animal model have been described in details and are used (Menendez L. et al. Brain Res. 969 (2003), 102-109) in these series of experiments.

a. Effects Induced by Compound 15 on Osteosarcoma-induced Thermal Hyperalgesia

Figure 4A:
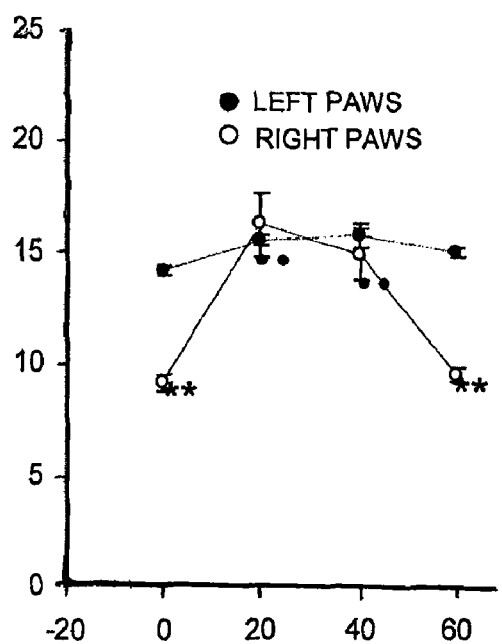
Figure 4B:
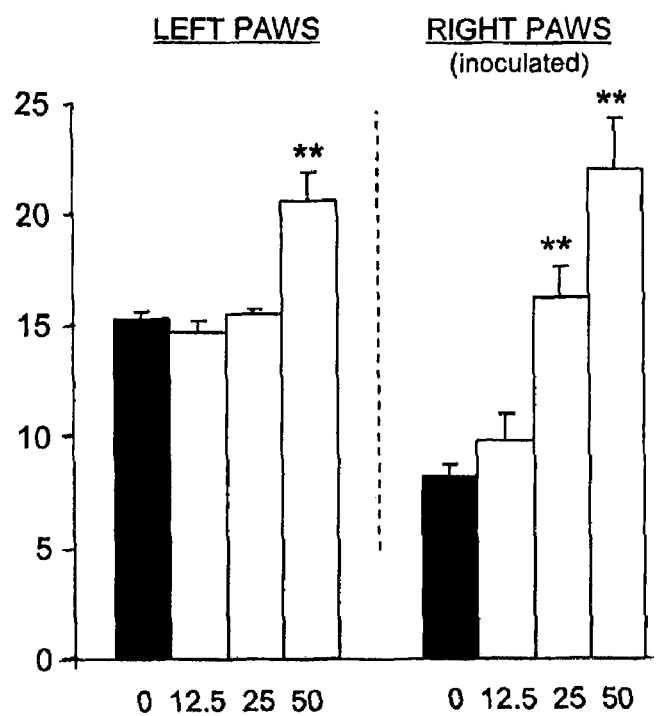

Osteosarcoma-induced thermal hyperalgesia measured by the unilateral hot plate test was inhibited by the oral administration of compound 15 (25 mg/kg). This inhibitory effect peaked 20-40 min after compound 15 administration, disappearing at time 60 (FIG. 4A). A dose-response curve was constructed 20 min after its administration (FIG. 4B), showing that the administration of 25 mg/kg of compound 15 exclusively increases the latencies measured in the inoculated right paws, (□) previously shortened by the development of the osteosarcoma. ** p≦0.01, ☆ p≦0.01, □ right inoculated paw, ■ left control paw.

b. Effects Induced by Opioid Receptor Antagonists on the Inhibition of Osteosarcoma-induced Thermal Hyperalgesia by Compound 15

The antihyperalgesic effect induced by 25 mg/kg of compound 15 (p.o., 20 minutes before testing) in the unilateral hot plate test was completely inhibited by the administration of naloxone-methiodide (2 mg/kg i.p., 20 min before testing, FIG. 5). At this concentration the antagonist is unable to enter the brain supporting a peripheral analgesic effects of compound 15. ** p≦0.01.

c. Effects of Gabapentin on Osteosarcoma-induced Thermal Hyperalgesia.

No modification of withdrawal latencies was detected 20 min after the i.p. administration of 25 mg/kg of Gabapentin to osteosarcoma-bearing mice. In contrast, a clear antihyperalgesic effect was detected 40 and 60 min after injection (FIG. 6A). Next, the antihyperalgesic effects induced by different doses of Gabapentin were measured 60 minutes after i.p. injection. The dose of 6.25 mg/kg of Gabapentin was subeffective, whereas the administration of 12.5 mg/kg produced a significant antihyperalgesic effect and a greater dose (25 mg/kg) completely suppressed the hyperalgesic effect induced by the osteosarcoma (FIG. 6B)

None of these doses of Gabapentin modified the withdrawal latencies of contralateral paws. ○ right inoculated paw, ● left control paw, ** p≦0.01.

d. Potentiation of the Antihyperalgesic Effect Induced by Compound 15 in Osteoarcoma-bearing Mice by the Coadministration of Gabapentin.

Figure 7A:
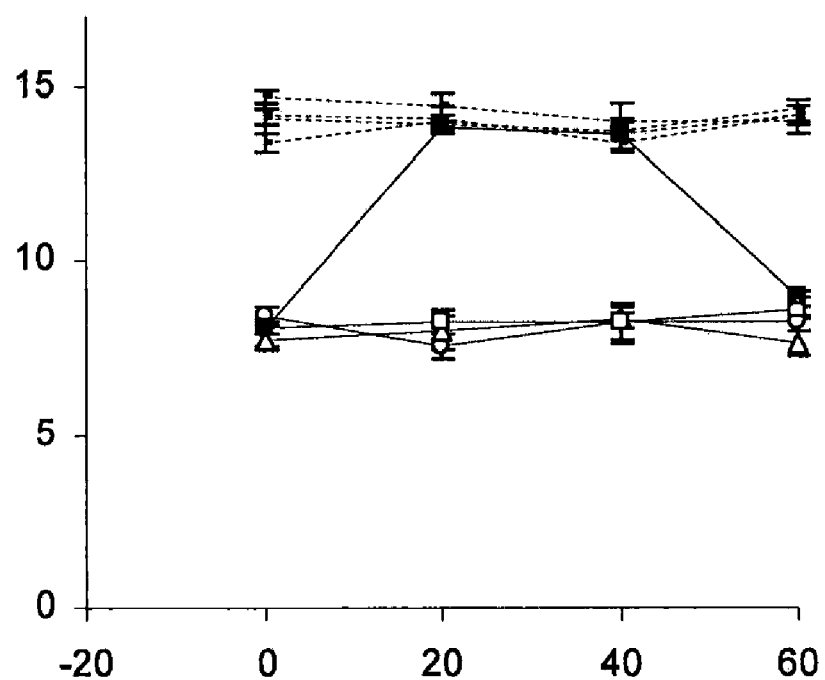
Figure 7B:
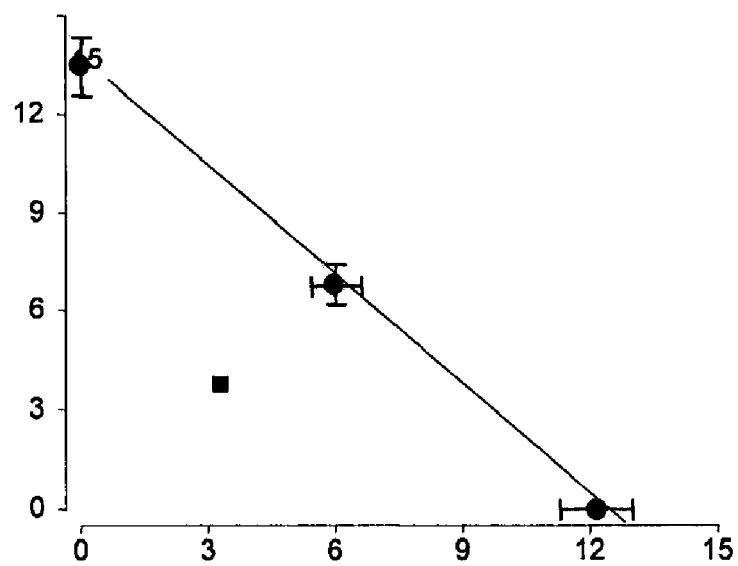

According to the results shown above, the acute administration of compound 15 (Δ) (12.5 mg/kg, 20 min before testing) or of Gabapentin (□) (6.25 mg/kg, 60 min before testing) do not produce any antihyperalgesic effect when administered alone. In contrast, when mice received 12.5 mg/kg of compound 15 (20 min before testing) plus 6.25 mg/kg of Gabapentin (60 min before testing) (■) osteosarcoma-induced thermal hyperalgesia was completely inhibited, being withdrawal latencies measured in osteosarcoma-bearing limbs undistinguishable from those obtained in the unaffected ones (discontinued line)(FIG. 7A). An isobolographic analysis was performed by studying the effects of the combination of different doses of both drugs (FIG. 7B).

The experimental ED50 value (■) was significantly lower (Student t test) than the theoretical ED50 value (●) (FIG. 7B) obtained if a purely additive interaction would occur, demonstrating that the antihyperalgesic effect produced by these drugs in combination is not additive. A further analysis shows that the interaction index is lower than 1, a value that indicates a synergistic interaction in which a twofold increase of the potency of the combination occurs (Tallarida R. J., Pain 98 (2002) 163-168).

The results obtained by the coadministration of compound 15 and Gabapentin indicate that the analgesic effects induced by both drugs are strongly potentiated in such a way that doses of both drugs ineffective if administered alone completely abolish osteosarcoma-induced hyperalgesia when associated. In fact, data obtained by the isolobographic analysis show that the experimental ED50 value obtained is significantly lower than the calculated theoretical ED50 value indicating a synergistic interaction (Tallarida R. J., Pain 98 (2002), 163-168). The present results constitute the first study describing that a synergistic interaction between Gabapentin and opiates may be obtained by using an inhibitor of enkephalin catabolism.

Overall, we show here that the oral administration of low doses of compound 15, an inhibitor of enkephalin-degrading enzymes, may inhibit osteosarcoma-induced thermal hyperalgesia acting peripherally. Furthermore, this peripheral thermal antihyperalgesic effect induced by compound 15 may be potentiated by the simultaneous administration of Gabapentin, in such a way that doses of both drugs that are separately inactive become active when simultaneously administered. These results reinforce the interest for the development of dual inhibitors of enkephalin inactivating peptidases as new analgesics devoid of the drawbacks of morphine and surrogates mainly due to the ubiquitous stimulation of the widely distributed opioid receptors by exogenous opioid receptor agonists.

The invention claimed is:

1. A pharmaceutical composition, wherein it comprises:
(a) at least one compound of the following formula (I):

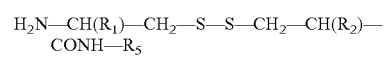

$H_2N-CH(R_1)-CH_2-S-S-CH_2-CH(R_2)-CONH-R_5$ wherein:

$R_1$ represents:

a hydrocarbon chain, saturated or unsaturated, linear or branched, comprising from 1 to 6 carbon atoms, optionally substituted by:
  an OR, SR or S(O)R radical, wherein in each of these radicals R represents a hydrogen, a linear or branched hydrocarbon chain of 1 to 4 carbon atoms, a phenyl or benzyl radical,
  a phenyl or benzyl radical,
a phenyl or benzyl radical optionally substituted by:
  1 to 5 halogens,
  an OR, SR or S(O)R radical, wherein in each of these radicals R is defined as above,
a methylene radical substituted by a 5- or 6-atom heterocycle, aromatic or saturated, having as a heteroatom an atom of nitrogen or sulfur, optionally oxidized in the form of N-oxide or S-oxide;

$R_2$ represents:
a phenyl or benzyl radical, optionally substituted by:
  1 to 5 halogen atoms, an OR or SR radical, wherein in each of these radicals R is defined as above,
an amino group optionally mono- or di-substituted by an aliphatic, cyclic or linear group of 1 to 6 carbon atoms,
a 5- or 6-atom aromatic ring, $R_5$ represents:
a $CH(R_3)$—COOR4 radical wherein
$R_3$ represents:
hydrogen,
an OH or OR group, with R as defined above,
a saturated hydrocarbon chain (alkyl), linear or branched, comprising from 1 to 6 carbon atoms, optionally substituted by an OR or SR radical, wherein in each of these radicals R is defined as above,
a phenyl or benzyl radical, optionally substituted by:
1 to 5 halogens,
an OR or SR radical, with R as defined above;
and
$OR_4$ represents an OCH(R")O(CO)OR', wherein:
R" represents
a hydrogen atom,
a C1-C6 alkyl chain, linear or branched, optionally substituted by a C1-C3 alkoxy group,
a C5-C8 cycloalkyl group,
a phenyl, benzyl, heteroaryl, alkylheteroaryl group, and
R' represents:
a saturated hydrocarbon chain (alkyl) with 1 to 6 carbon atoms, linear or branched and optionally substituted by a C1-C3 alkoxy group,
a C5-C8 cycloalkyl group,
a phenyl, benzyl, heteroaryl, alkylheteroaryl group;
and additive salts of the aforesaid compounds (I) with pharmaceutically acceptable mineral or organic acids;
(b) at least one compound selected from the group consisting of cannabinoid derivatives, morphine, morphine derivatives, Gabapentin and pregabalin; and
(c) a pharmaceutically suitable excipient.

2. A method for treating depression and pain, comprising the administration of an effective amount of the pharmaceutical composition according to claim 1 to a patient in need thereof.

3. A method for treating depression and pain comprising the administration of an effective amount of a combination of a compound of the following formula (I):

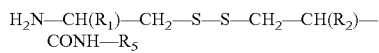

wherein:
$R_1$ represents:
a hydrocarbon chain, saturated or unsaturated, linear or branched, comprising from 1 to 6 carbon atoms, optionally substituted by:
an OR, SR or S(O)R radical, wherein in each of these radicals R represents a hydrogen, a linear or branched hydrocarbon chain of 1 to 4 carbon atoms, a phenyl or benzyl radical,
a phenyl or benzyl radical,
a phenyl or benzyl radical optionally substituted by:
1 to 5 halogens,
an OR, SR or S(O)R radical, wherein in each of these radicals R is defined as above,
a methylene radical substituted by a 5- or 6-atom heterocycle, aromatic or saturated, having as a heteroatom an atom of nitrogen or sulfur, optionally oxidized in the form of N-oxide or S-oxide;

$R_2$ represents:
a phenyl or benzyl radical, optionally substituted by:
1 to 5 halogen atoms,
an OR or SR radical, wherein in each of these radicals R is defined as above,
an amino group optionally mono- or di-substituted by an aliphatic, cyclic or linear group of 1 to 6 carbon atoms,
a 5- or 6-atom aromatic ring, $R_5$ represents:
a $CH(R_3)$—COOR4 radical wherein
$R_3$ represents:
hydrogen,
an OH or OR group, with R as defined above,
a saturated hydrocarbon chain (alkyl), linear or branched, comprising from 1 to 6 carbon atoms, optionally substituted by an OR or SR radical, wherein in each of these radicals R is defined as above,
a phenyl or benzyl radical, optionally substituted by:
1 to 5 halogens,
an OR or SR radical, with R as defined above; and
$OR_4$ represents an OCH(R")O(CO)OR', wherein:
R" represents
a hydrogen atom,
a C1-C6 alkyl chain, linear or branched, optionally substituted by a C1-C3 alkoxy group,
a C5-C8 cycloalkyl group,
a phenyl, benzyl, heteroaryl, alkylheteroaryl group, and
R' represents:
a saturated hydrocarbon chain (alkyl) with 1 to 6 carbon atoms, linear or branched and optionally substituted by a C1-C3 alkoxy group,
a C5-C8 cycloalkyl group,
a phenyl, benzyl, heteroaryl, alkylheteroaryl group;
and additive salts of the aforesaid compounds (I) with pharmaceutically acceptable mineral or organic acids,
and at least one compound selected from the group consisting of cannabinoid derivatives, morphine, morphine derivatives, Gabapentin and pregabalin, to a patient in need thereof.

4. The pharmaceutical composition according to claim 1, wherein the at least one compound selected from the group consisting of cannabinoid derivatives, morphine, morphine derivatives, Gabapentin and pregabalin is a cannabinoid derivative.

5. The method according to claim 3, wherein the at least one compound selected from the group consisting of cannabinoid derivatives, morphine, morphine derivatives, Gabapentin and pregabalin is a cannabinoid derivative.

6. A pharmaceutical combination product, comprising:
i) a composition comprising at least one compound of the following formula (I), $H_2N$—$CH(R_1)$—$CH_2$—S—S—$CH_2$—$CH(R_2)$—CONH—$R_5$ wherein:
$R_1$ represents:
a hydrocarbon chain, saturated or unsaturated, linear or branched, comprising from 1 to 6 carbon atoms, optionally substituted by:
an OR, SR or S(O)R radical, wherein in each of these radicals R represents a hydrogen, a linear or branched hydrocarbon chain of 1 to 4 carbon atoms, a phenyl or benzyl radical,
a phenyl or benzyl radical,
a phenyl or benzyl radical optionally substituted by:
1 to 5 halogens, an OR, SR or S(O)R radical, wherein in each of these radicals R is defined as above,
a methylene radical substituted by a 5- or 6-atom heterocycle, aromatic or saturated, having as a heteroatom an atom of nitrogen or sulfur, optionally oxidized in the form of N-oxide or S-oxide;

$R_2$ represents:
a phenyl or benzyl radical, optionally substituted by:
1 to 5 halogen atoms,
an OR or SR radical, wherein in each of these radicals R is defined as above,
an amino group optionally mono- or di-substituted by an aliphatic, cyclic or linear group of 1 to 6 carbon atoms,
a 5- or 6-atom aromatic ring, $R_5$ represents:
a $CH(R_3)$—COOR4 radical wherein
$R_3$ represents:
hydrogen,
an OH or OR group, with R as defined above,
a saturated hydrocarbon chain (alkyl), linear or branched, comprising from 1 to 6 carbon atoms, optionally substituted by an OR or SR radical, wherein in each of these radicals R is defined as above,
a phenyl or benzyl radical, optionally substituted by:
1 to 5 halogens,
an OR or SR radical, with R as defined above; and
$OR_4$ represents an OCH(R")O(CO)OR', wherein:
R" represents
a hydrogen atom,
a C1-C6 alkyl chain, linear or branched, optionally substituted by a C1-C3 alkoxy group,
a C5-C8 cycloalkyl group,
a phenyl, benzyl, heteroaryl, alkylheteroaryl group, and
R' represents:
a saturated hydrocarbon chain (alkyl) with 1 to 6 carbon atoms, linear or branched and optionally substituted by a C1-C3 alkoxy group,
a C5-C8 cycloalkyl group,
a phenyl, benzyl, heteroaryl, alkylheteroaryl group;
and additive salts of the aforesaid compounds (I) with pharmaceutically acceptable mineral or organic acids,
ii) a composition comprising a compound selected from the group consisting of cannabinoid derivatives, morphine, morphine derivatives, Gabapentin and pregabalin, and combinations thereof;
wherein the compositions are suitable for simultaneous, separate or staggered use.

7. A method for treating depression and pain comprising the administration of an effective amount of a pharmaceutical composition comprising:
i) at least one compound of formula (I),

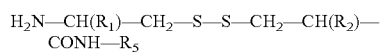

wherein:
$R_1$ represents:
a hydrocarbon chain, saturated or unsaturated, linear or branched, comprising from 1 to 6 carbon atoms, optionally substituted by:
an OR, SR or S(O)R radical, wherein in each of these radicals R represents a hydrogen, a linear or branched hydrocarbon chain of 1 to 4 carbon atoms, a phenyl or benzyl radical,
a phenyl or benzyl radical,
a phenyl or benzyl radical optionally substituted by:
1 to 5 halogens,
an OR, SR or S(O)R radical, wherein in each of these radicals R is defined as above,
a methylene radical substituted by a 5- or 6-atom heterocycle, aromatic or saturated, having as a heteroatom an atom of nitrogen or sulfur, optionally oxidized in the form of N-oxide or S-oxide;

$R_2$ represents:
a phenyl or benzyl radical, optionally substituted by:
1 to 5 halogen atoms,
an OR or SR radical, wherein in each of these radicals R is defined as above,
an amino group optionally mono- or di-substituted by an aliphatic, cyclic or linear group of 1 to 6 carbon atoms,
a 5- or 6-atom aromatic ring, $R_5$ represents:
a $CH(R_3)$—COOR4 radical wherein
$R_3$ represents:
hydrogen,
an OH or OR group, with R as defined above,
a saturated hydrocarbon chain (alkyl), linear or branched, comprising from 1 to 6 carbon atoms, optionally substituted by an OR or SR radical, wherein in each of these radicals R is defined as above,
a phenyl or benzyl radical, optionally substituted by:
1 to 5 halogens,
an OR or SR radical, with R as defined above; and
$OR_4$ represents an OCH(R")O(CO)OR', wherein:
R" represents
a hydrogen atom,
a C1-C6 alkyl chain, linear or branched, optionally substituted by a C1-C3 alkoxy group,
a C5-C8 cycloalkyl group,
a phenyl, benzyl, heteroaryl, alkylheteroaryl group, and
R' represents:
a saturated hydrocarbon chain (alkyl) with 1 to 6 carbon atoms, linear or branched and optionally substituted by a C1-C3 alkoxy group,
a C5-C8 cycloalkyl group,
a phenyl, benzyl, heteroaryl, alkylheteroaryl group;
and additive salts of the aforesaid compounds (I) with pharmaceutically acceptable mineral or organic acids, and
ii) at least one compound selected from the group consisting of cannabinoid derivatives, morphine, morphine derivatives, Gabapentin and pregabalin as combination products for simultaneous, separate or staggered use, to a patient in need thereof.

8. The pharmaceutical composition according to claim 1, wherein the at least one compound selected from the group consisting of cannabinoid derivatives, morphine, morphine derivatives, Gabapentin and pregabalin is morphine or a morphine derivative.

9. The method according to claim 3, wherein the at least one compound selected from the group consisting of cannabinoid derivatives, morphine, morphine derivatives, Gabapentin and pregabalin is morphine or a morphine derivative.

10. The pharmaceutical composition according to claim 1, wherein the at least one compound selected from the group consisting of cannabinoid derivatives, morphine, morphine derivatives, Gabapentin and pregabalin is Gabapentin or pregabalin.

11. The method according to claim 3, wherein the at least one compound selected from the group consisting of cannabinoid derivatives, morphine, morphine derivatives, Gabapentin and pregabalin is Gabapentin or pregabalin.

12. The pharmaceutical composition according to claim 1, wherein one or more of $R_1$, $R_2$ and $R_5$ is a phenyl or benzyl radical substituted with fluorine.

13. The pharmaceutical composition according to claim 1, wherein R' is a C1-C4 alkyl group optionally substituted by a methoxy group, or a C5-C6 cycloalkyl group.

14. The pharmaceutical composition according to claim 1, wherein R" is: a C1-C4 alkyl group, optionally substituted with a methoxy group; or a C5-C6 cycloalkyl group.

15. The pharmaceutical composition according to claim 1, wherein the pharmaceutically suitable excipient is suitable for oral, nasal or intravenous administration.

16. The pharmaceutical combination product according to claim 6, wherein one or more of $R_1$, $R_2$ and $R_5$ is a phenyl or benzyl radical substituted with fluorine.

17. The pharmaceutical combination product according to claim 6, wherein one or more of R" is a C1-C4 alkyl group optionally substituted by a methoxy group, or a C5-C6 cycloalkyl group.

18. The pharmaceutical combination product according to claim 6, wherein R' is: a C1-C4 alkyl group, optionally substituted with a methoxy group; or a C5-C6 cycloalkyl group.

19. The pharmaceutical composition according to claim 4, wherein the cannabinoid derivatives is $\Delta^9$-tetrahydrocannabinol.

20. The pharmaceutical composition according to claim 8, wherein the at least one compound selected from the group consisting of cannabinoid derivatives, morphine, morphine derivatives, Gabapentin and pregabalin is morphine.

21. The pharmaceutical composition according to claim 1, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

22. The pharmaceutical composition according to claim 4, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

23. The pharmaceutical combination product according to claim 6, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

24. The pharmaceutical composition according to claim 8, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

25. The pharmaceutical composition according to claim 10, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

26. The pharmaceutical combination product according to claim 6, wherein the at least one compound selected from the group consisting of cannabinoid derivatives, morphine, morphine derivatives, Gabapentin and pregabalin is a cannabinoid derivative.

27. The pharmaceutical combination product according to claim 26, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

28. The pharmaceutical combination product according to claim 26, wherein the cannabinoid derivatives is $\Delta^9$-tetrahydrocannabinol.

29. The pharmaceutical combination product according to claim 6, wherein the at least one compound selected from the group consisting of cannabinoid derivatives, morphine, morphine derivatives, Gabapentin and pregabalin is morphine or a morphine derivative.

30. The pharmaceutical combination product according to claim 29, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

31. The pharmaceutical combination product according to claim 29, wherein the morphine or morphine derivative is morphine.

32. The pharmaceutical combination product according to claim 6, wherein the at least one compound selected from the group consisting of cannabinoid derivatives, morphine, morphine derivatives, Gabapentin and pregabalin is Gabapentin or pregabalin.

33. The pharmaceutical combination product according to claim 32, wherein the at least one compound of formula (I) is: 1-(2-((1-ethoxycarbonyloxy-ethoxycarbonylmethyl)-carbamoyl)-3-phenyl-propyldisulfanylmethyl)-3-methylsulfanylpropyl-amine.

34. The method of claim 2, wherein the pain is selected from the group consisting of acute pain, nociceptive pain, inflammatory pain or neurogenic pain.

35. The method of claim 5, wherein the cannabinoid derivative is $\Delta^9$-tetrahydrocannabinol.

* * * * *